US012345710B2

(12) United States Patent
Kang et al.

(10) Patent No.: US 12,345,710 B2
(45) Date of Patent: Jul. 1, 2025

(54) MARKER FOR DIAGNOSING COLORECTAL CANCER AND METHOD FOR PROVIDING INFORMATION REQUIRED FOR DIAGNOSIS OF COLORECTAL CANCER

(71) Applicant: SAMSUNG LIFE PUBLIC WELFARE FOUNDATION, Seoul (KR)

(72) Inventors: Eun Suk Kang, Seoul (KR); Hee Cheol Kim, Seoul (KR); Jae Won Yun, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 911 days.

(21) Appl. No.: 17/594,925

(22) PCT Filed: Apr. 29, 2020

(86) PCT No.: PCT/KR2020/005778
§ 371 (c)(1),
(2) Date: Nov. 3, 2021

(87) PCT Pub. No.: WO2020/226366
PCT Pub. Date: Nov. 12, 2020

(65) Prior Publication Data
US 2022/0221462 A1 Jul. 14, 2022

(30) Foreign Application Priority Data
May 3, 2019 (KR) .................. 10-2019-0052556

(51) Int. Cl.
*G01N 33/574* (2006.01)
*G01N 1/30* (2006.01)

(52) U.S. Cl.
CPC ......... *G01N 33/57446* (2013.01); *G01N 1/30* (2013.01); *G01N 2440/14* (2013.01)

(58) Field of Classification Search
CPC ....... G01N 2440/14; G01N 2333/5412; G01N 2333/5428; G01N 2800/52
See application file for complete search history.

(56) References Cited

U.S. PATENT DOCUMENTS

2006/0127502 A1 6/2006 Yu et al.
2012/0021941 A1 1/2012 Heimberger

FOREIGN PATENT DOCUMENTS

JP 2013525786 A 6/2013
JP 2019066482 A 4/2019
WO WO-2012/078982 A2 6/2012

OTHER PUBLICATIONS

Xiao J. Cell Mol Med 2017 21:286-298 (Year: 2017).*
Extended European Search Report from corresponding European Patent Application No. 20801458.9, issued on Jun. 22, 2022.
Ji, K., et al.; "The Role of p-STAT3 as a Prognostic and Clinicopathological Marker in Colorectal Cancer: A Systematic Review and Meta-Analysis", PLOS One, vol. 11, No. 8, Sep. 9, 2016, pp. 1-16.
Yeh, K., et al.: "Colorectal cancer cell-derived interleukin-6 enhances the phagocytic capacity and migration of THP-1 cells", Cytokine, 79, 2016, pp. 82-89.
Park, J. H., et al.; "Signal Transduction and Activator of Transcription-3 (STAT3) in Patients with Colorectal Cancer: Associations with the Phenotypic Features of the Tumor and Host", Clinical Cancer Research, vol. 23, No. 7, Sep. 27, 2016, pp. 1698-1709.
International Search Report from corresponding PCT Application No. PCT/KR2020/005778, dated Sep. 17, 2020.
Ma, X., et al.; "Constitutive activation of Stat3 signaling pathway in human colorectal carcinoma", World J Gastroenterol 2004;10(11):1569-1573.
Wu, W. , et al.; "STAT3 activation in monocytes accelerates liver cancer progression", BMC Cancer 2011, 11:506, pp. 1-10.

* cited by examiner

*Primary Examiner* — Changhwa J Cheu
(74) *Attorney, Agent, or Firm* — Harness, Dickey & Pierce, P.L.C.

(57) ABSTRACT

The present invention relates to a marker for diagnosing colorectal cancer, a method for providing information required for the diagnosis of colorectal cancer by using same, and a method for providing information for monitoring the response to colorectal cancer therapy by using same.

11 Claims, 13 Drawing Sheets

MARKER FOR DIAGNOSING COLORECTAL CANCER AND METHOD FOR PROVIDING INFORMATION REQUIRED FOR DIAGNOSIS OF COLORECTAL CANCER

CROSS-REFERENCE TO RELATED APPLICATIONS

This application is a national phase application of PCT Application No. PCT/KR2020/005778, filed on 29 Apr. 2020, which claims the benefit and priority to Korean Patent Application No. 10-2019-0052556, filed on 3 May 2019. The entire disclosures of the applications identified in this paragraph are incorporated herein by references.

TECHNICAL FIELD

This application claims priority to and the benefit of Korean Patent Application No. 10-2019-0052556 filed in the Korean Intellectual Property Office on 3 May 2019, the disclosure of which is incorporated herein by reference.

The present disclosure relates to a marker for diagnosing colorectal cancer, a method for providing information required for the diagnosis of colorectal cancer by using the same, and a method for providing information for monitoring a therapeutic response of colorectal cancer by using the same.

BACKGROUND ART

Typically, a colonoscopy is mainly performed to examine for the presence or absence of colorectal cancer. However, a bowel emptying procedure was needed to perform the colonoscopy. Accordingly, though a colonoscopy has been recommended for colorectal cancer screening, only some subjects get examined due to the above inconvenience in the procedure. Moreover, a colonoscopy may cause some serious side effects, such as bowel perforation or bowel bleeding. A stool occult blood test has also been used as a screening test, but has a disadvantage of low sensitivity.

A diagnostic marker capable of identifying the presence or absence of colorectal cancer through a blood test is known to detect CEA protein in blood. However, the sensitivity changes depending on the stage of disease, for example, about 30% at stages 1 and 2 and 75% or more at stages 3 and 4, and thus such a diagnostic marker is less useful for a screening test. Except for these, nothing has been well established so far. Recently, with the development of molecular genetic techniques, blood-based cancer diagnosis methods using circulating tumor DNA (ctDNA) and exosomes are being actively studied. However, these methods can provide increased usability and optimized performance only when specific targets are defined.

Therefore, there is a need for an examination that has few side effects, is easily performed by simple blood collection or the like, and has high diagnostic sensitivity. Signal transducer and activator of transcription (STAT) proteins are subordinate transcription factors of the JAK signaling system, and are known to be STAT 1, 2, 3, 4, 5A, 5B, and 6. Each STAT protein is activated through phosphorylation by specific cytokine stimulation and the reaction between receptors thereof to induce cytokine secretion through signaling to nuclei, and is involved in the differentiation, survival, and activity of cells, especially, immune cells. As a method for examining the STAT phosphorylation response to cytokine stimulation in blood immune cells through phospho-flow analysis, an examination is performed by simple blood collection and the results thereof can be obtained within one day. In addition, the phosphorylation levels of several STAT proteins in various immune cells are identified using the advantages of flow cytometry, thereby providing immunological and clinical significances.

SUMMARY

Technical Problem

Accordingly, an aspect of the present disclosure is to provide a marker for diagnosing colorectal cancer.

Another aspect of the present disclosure is to provide information required for the diagnosis of colorectal cancer.

Still another aspect of the present disclosure is to provide a method for providing information for monitoring a therapeutic response of colorectal cancer.

Solution to Problem

The present disclosure relates to a marker for diagnosing colorectal cancer, a method for providing information required for the diagnosis of colorectal cancer by using the same, and a method for providing information for monitoring a therapeutic response of colorectal cancer by using the same.

Hereinafter, the present disclosure will be described in more detail.

An aspect of the present disclosure is directed to a method for providing information required for the diagnosis of colorectal cancer, the method including:

measuring the level of STAT3 phosphorylation in Th cells contained in a first sample; and measuring the level of STAT3 phosphorylation in Tc cells contained in a second sample.

In the present disclosure, the first sample may be obtained from organs, tissues, and cells of a subject. The first sample may include lymphocytes, and for example, may include peripheral blood, but is not limited thereto.

In the present disclosure, the first sample may be prepared by the following steps:

a mononuclear cells isolation step of isolating mononuclear cells contained in blood;

a cytokine treatment step of treating the isolated mononuclear cells with a cytokine; and a phosphorylation staining step of performing phosphorylation staining.

In the present disclosure, the cytokine with which the first sample is treated may be IL-10.

In the present disclosure, the concentration of the IL-10 may be 9.0 to 11.0 ng/ml, 9.0 to 10.8 ng/ml, 9.0 to 10.6 ng/ml, 9.0 to 10.4 ng/ml, 9.0 to 10.2 ng/ml, 9.2 to 11.0 ng/ml, 9.2 to 10.8 ng/ml, 9.2 to 10.6 ng/ml, 9.2 to 10.4 ng/ml, 9.2 to 10.2 ng/ml, 9.4 to 11.0 ng/ml, 9.4 to 10.8 ng/ml, 9.4 to 10.6 ng/ml, 9.4 to 10.4 ng/ml, 9.4 to 10.2 ng/ml, 9.6 to 11.0 ng/ml, 9.6 to 10.8 ng/ml, 9.6 to 10.6 ng/ml, 9.6 to 10.4 ng/ml, 9.6 to 10.2 ng/ml, 9.8 to 11.0 ng/ml, 9.8 to 10.8 ng/ml, 9.8 to 10.6 ng/ml, 9.8 to 10.4 ng/ml, or 9.8 to 10.2 ng/ml, and for example, 10.0 ng/ml.

In the present disclosure, the second sample may be obtained from organs, tissues, and cells of a subject. The second sample may include lymphocytes, and for example, may include peripheral blood, but are not limited thereto.

In the present disclosure, the second sample may be prepared by the following steps:

a mononuclear cell isolation step of isolating mononuclear cells contained in blood;

a cytokine treatment step of treating the isolated mononuclear cells with a cytokine; and a phosphorylation staining step of performing phosphorylation staining.

In the present disclosure, the cytokine with which the second sample is treated may be IL-6.

In the present disclosure, the concentration of the IL-6 may be 19.0 to 21.0 ng/ml, 19.0 to 20.8 ng/ml, 19.0 to 20.6 ng/ml, 19.0 to 20.4 ng/ml, 19.0 to 20.2 ng/ml, 19.2 to 21.0 ng/ml, 19.2 to 20.8 ng/ml, 19.2 to 20.6 ng/ml, 19.2 to 20.4 ng/ml, 19.2 to 20.2 ng/ml, 19.4 to 21.0 ng/ml, 19.4 to 20.8 ng/ml, 19.4 to 20.6 ng/ml, 19.4 to 20.4 ng/ml, 19.4 to 20.2 ng/ml, 19.6 to 21.0 ng/ml, 19.6 to 20.8 ng/ml, 19.6 to 20.6 ng/ml, 19.6 to 20.4 ng/ml, 19.6 to 20.2 ng/ml, 19.8 to 21.0 ng/ml, 19.8 to 20.8 ng/ml, 19.8 to 20.6 ng/ml, 19.8 to 20.4 ng/ml, or 19.8 to 20.2 ng/ml, and for example, 20.0 ng/ml, but is not limited thereto.

In the present disclosure, the measuring of the level of STAT3 phosphorylation is performed using flow cytometry, but is not limited thereto.

Another aspect of the present disclosure is directed to a method for providing information for monitoring a therapeutic response of colorectal cancer, the method including:

measuring the level of STAT3 phosphorylation in Th cells contained in a first sample; and measuring the level of STAT3 phosphorylation in Tc cells contained in a second sample.

In the present disclosure, the first sample may be obtained from organs, tissues, and cells of a subject. The first sample may include lymphocytes, and for example, may include peripheral blood, but are not limited thereto.

In the present disclosure, the first sample may be prepared by the following steps:

a mononuclear cell isolation step of isolating mononuclear cells contained in blood;

a cytokine treatment step of treating the isolated mononuclear cells with a cytokine; and a phosphorylation staining step of performing phosphorylation staining.

In the present disclosure, the cytokine with which the first sample is treated may be IL-10.

In the present disclosure, the concentration of the IL-10 may be 9.0 to 11.0 ng/ml, 9.0 to 10.8 ng/ml, 9.0 to 10.6 ng/ml, 9.0 to 10.4 ng/ml, 9.0 to 10.2 ng/ml, 9.2 to 11.0 ng/ml, 9.2 to 10.8 ng/ml, 9.2 to 10.6 ng/ml, 9.2 to 10.4 ng/ml, 9.2 to 10.2 ng/ml, 9.4 to 11.0 ng/ml, 9.4 to 10.8 ng/ml, 9.4 to 10.6 ng/ml, 9.4 to 10.4 ng/ml, 9.4 to 10.2 ng/ml, 9.6 to 11.0 ng/ml, 9.6 to 10.8 ng/ml, 9.6 to 10.6 ng/ml, 9.6 to 10.4 ng/ml, 9.6 to 10.2 ng/ml, 9.8 to 11.0 ng/ml, 9.8 to 10.8 ng/ml, 9.8 to 10.6 ng/ml, 9.8 to 10.4 ng/ml, or 9.8 to 10.2 ng/ml, and for example, 10.0 ng/ml, but is not limited thereto.

In the present disclosure, the second sample may be obtained from organs, tissues, and cells of a subject. The second sample may include lymphocytes, and for example, may include peripheral blood, but are not limited thereto.

In the present disclosure, the second sample may be prepared by the following steps:

a mononuclear cell isolation step of isolating mononuclear cells contained in blood;

a cytokine treatment step of treating the isolated mononuclear cells with a cytokine; and a phosphorylation staining step of performing phosphorylation staining.

In the present disclosure, the cytokine with which the second sample is treated may be IL-6.

In the present disclosure, the concentration of the IL-6 may be 19.0 to 21.0 ng/ml, 19.0 to 20.8 ng/ml, 19.0 to 20.6 ng/ml, 19.0 to 20.4 ng/ml, 19.0 to 20.2 ng/ml, 19.2 to 21.0 ng/ml, 19.2 to 20.8 ng/ml, 19.2 to 20.6 ng/ml, 19.2 to 20.4 ng/ml, 19.2 to 20.2 ng/ml, 19.4 to 21.0 ng/ml, 19.4 to 20.8 ng/ml, 19.4 to 20.6 ng/ml, 19.4 to 20.4 ng/ml, 19.4 to 20.2 ng/ml, 19.6 to 21.0 ng/ml, 19.6 to 20.8 ng/ml, 19.6 to 20.6 ng/ml, 19.6 to 20.4 ng/ml, 19.6 to 20.2 ng/ml, 19.8 to 21.0 ng/ml, 19.8 to 20.8 ng/ml, 19.8 to 20.6 ng/ml, 19.8 to 20.4 ng/ml, or 19.8 to 20.2 ng/ml, and for example, 20.0 ng/ml, but is not limited thereto.

In the present disclosure, the subject may be a patient who is being treated for colorectal cancer, for example, a patient who has undergone colorectal cancer surgery. The method for providing information for monitoring of the present disclosure cannot be employed for patients receiving chemoimmunotherapy or immunotherapy for colorectal cancer treatment.

In the present disclosure, the measuring of the level of STAT3 phosphorylation is performed using flow cytometry, but is not limited thereto.

In the present disclosure, the "Th cells" refers to helper T cells, also known as CD4+ cells or CD4-positive cells, which are cells playing an important role in the action of the immune system and are a kind of lymphocyte. Th cells usually do not have cytotoxic activity and cannot directly kill infected (somatic) cells or antigens. The helper T cells (Th cells) serve to activate and direct other immune cells, and especially play a very important role in the immune system. The helper T cells are essential for antibody production by B cells, activation of cytotoxic T cells, promotion of antibacterial activity of phagocytes including macrophages, and the like. The naming of helper T cells or assisting T cells is also due to the fact that they help a lot in the activities of other cells.

In the present disclosure, the term "Tc cells" refers to cytotoxic T cells (CD8+, Tc), which are a kind of lymphocyte and can destroy somatic or tumor cells infected with viruses. Cytotoxic T cells eliminate the cells infected with antigens such as viruses, damaged or malfunctioning cells, and the like. Most cytotoxic T cells have T cell receptors (TCRs) and thus can recognize specific antigenic peptides attached to the type I MHC molecules located on the surface of all cells. In addition, a glycoprotein called CD8 is located on the surface of cytotoxic T cells to bind to a constant region of the type I MHC molecule. The binding between CD8 and the MHC molecule further enhances the binding between cytotoxic T cells (TC) and target cells. CD8+ T cells appear to usually perform predetermined cytotoxic activity in the immune system.

Advantageous Effects of Invention

The present disclosure relates to a marker for diagnosing colorectal cancer, a method for providing information required for the diagnosis of colorectal cancer by using the same, and a method for providing information for monitoring a therapeutic response of colorectal cancer by using the same, wherein the marker and the methods have effects of significantly improving diagnostic sensitivity and specificity.

BEST MODE FOR CARRYING OUT THE INVENTION

Figure 1:
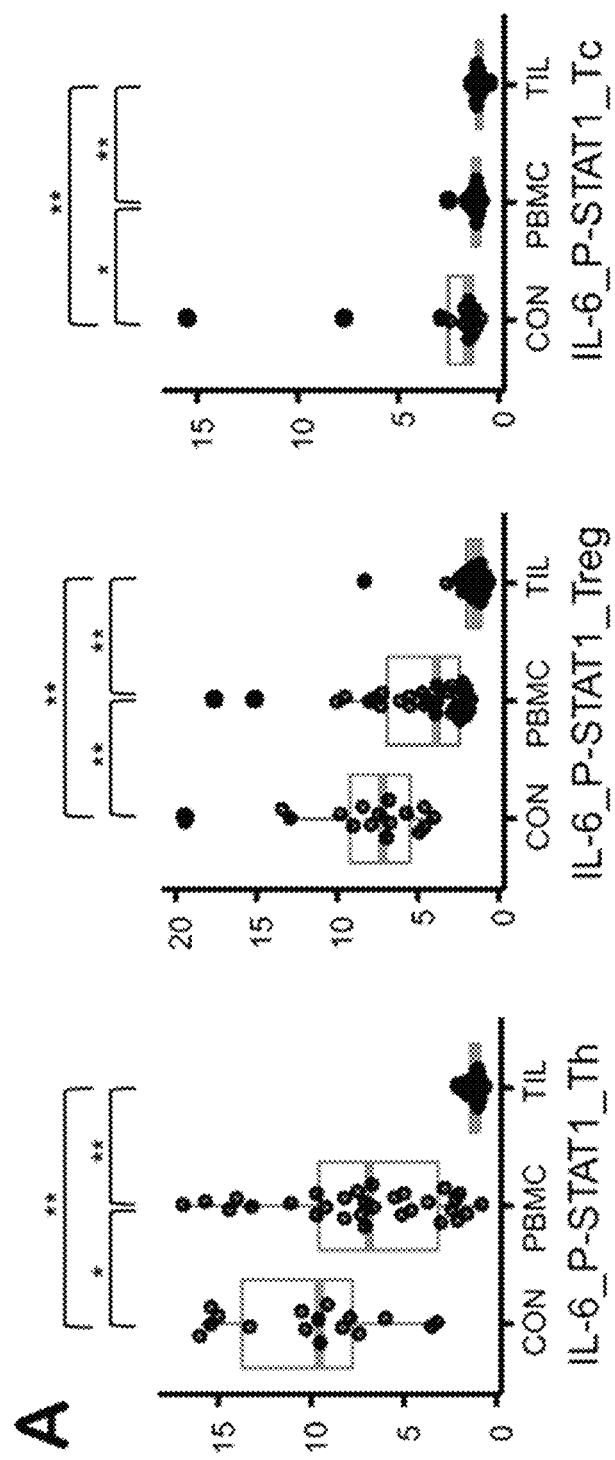
FIG. 1 is a graph showing the results that there were differences in STAT1 phosphorylation by IL-6 stimulation in the blood immune cells of healthy persons and the blood immune cells and tumor immune cells of cancer patients according to an embodiment of the present disclosure.
Figure 2:
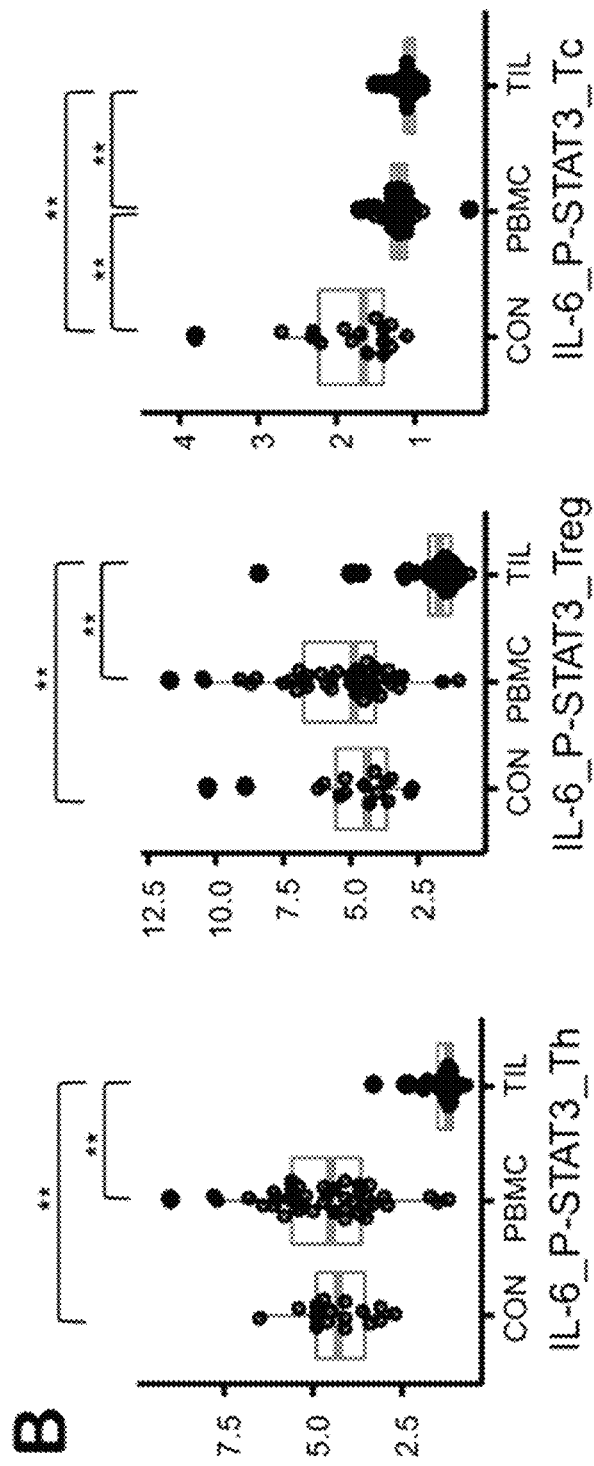
FIG. 2 is a graph showing the results that there was a difference in STAT3 phosphorylation by IL-6 stimulation in the blood immune cells of healthy person and the blood immune cells and tumor immune cells of cancer patients.
Figure 3:
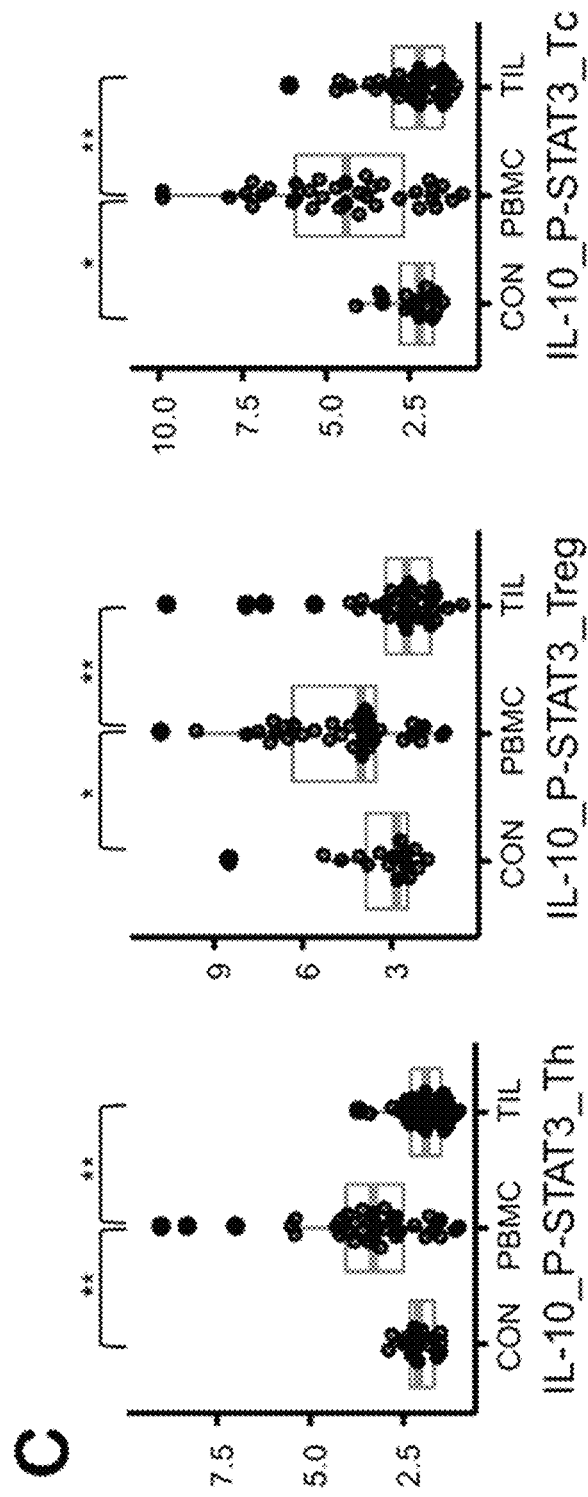
FIG. 3 is a graph showing the results that there was a difference in STAT3 phosphorylation by IL-10 stimulation in the blood immune cells of healthy person and the blood immune cells and tumor immune cells of cancer patients.
Figure 4:
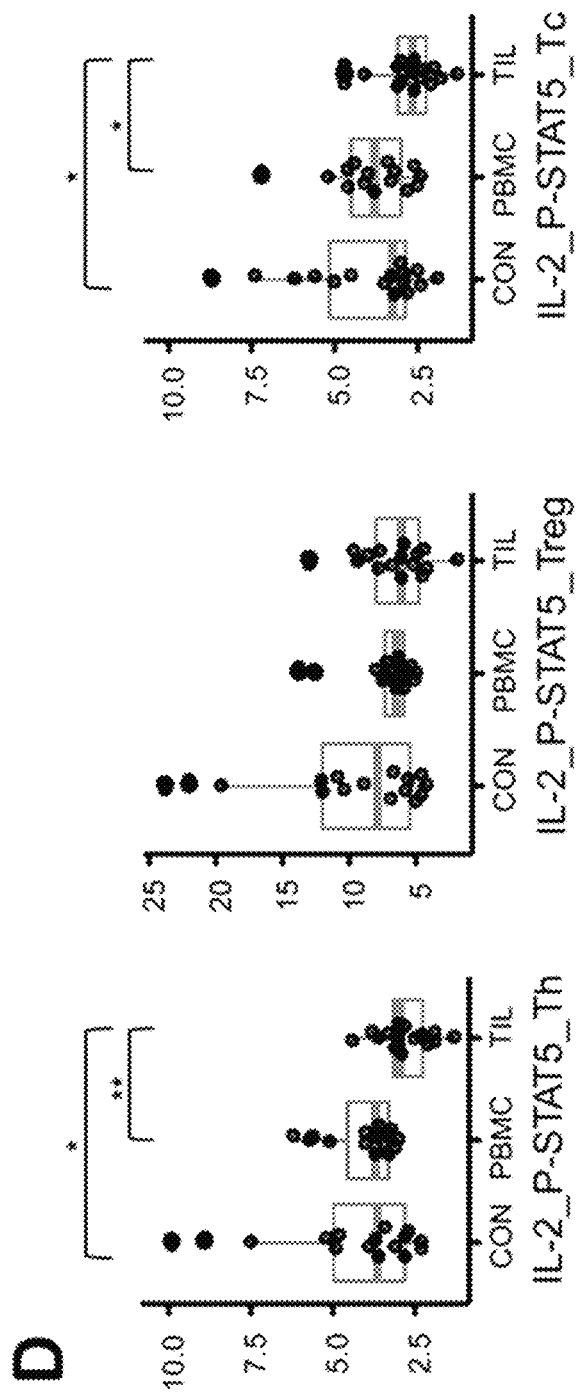
FIG. 4 is a graph showing the results that there was a difference in STAT5 phosphorylation by IL-2 stimulation in the blood immune cells of healthy person and the blood immune cells and tumor immune cells of cancer patients.
Figure 5:
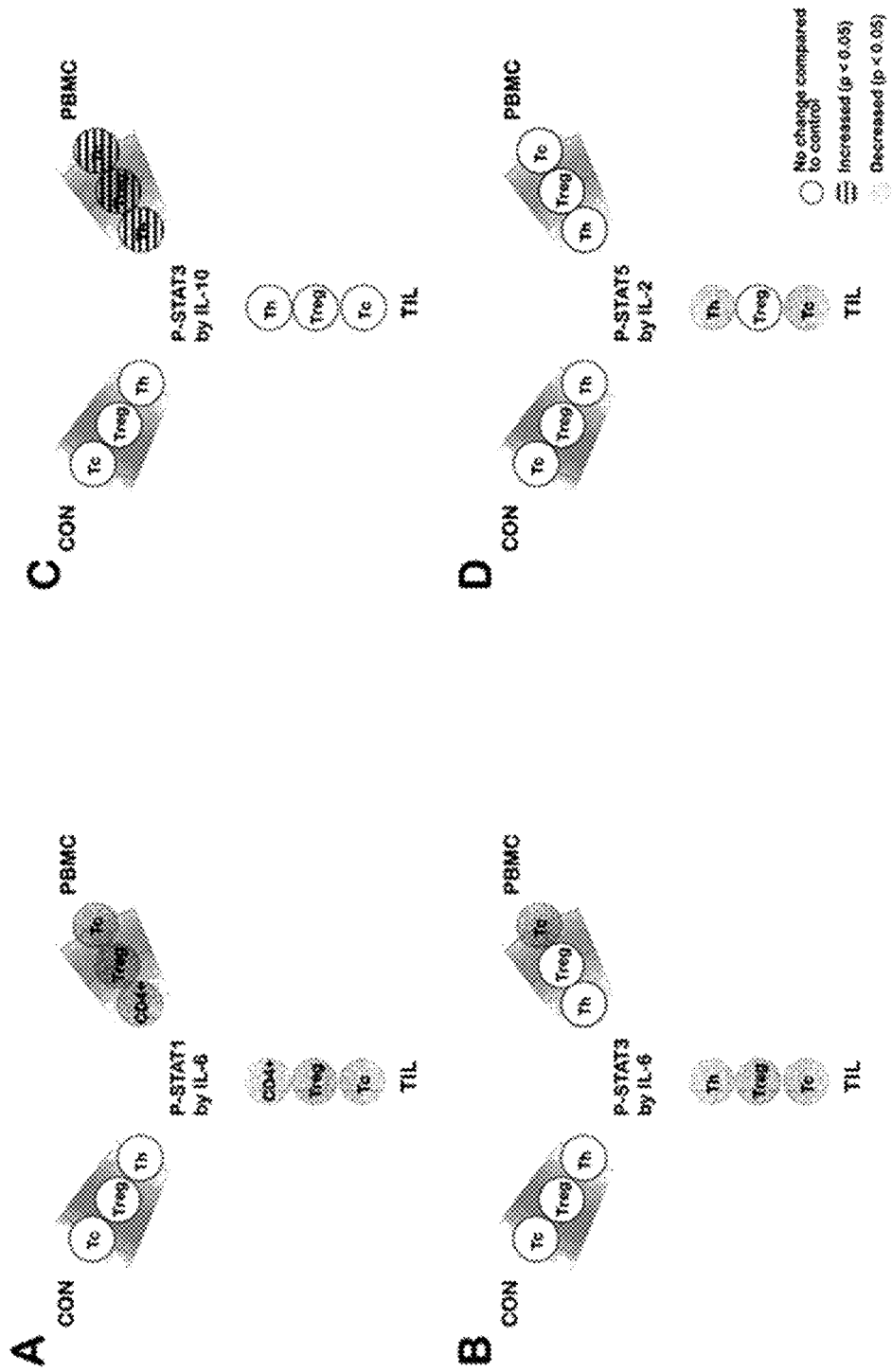
FIG. 5 is a schematic diagram showing changes in values in the blood immune cells and tumor immune cells of cancer patients by using the values in the blood immune cells of healthy persons as base values, from the results in FIGS. 1 to 4 according to an embodiment of the present disclosure.

A method for providing information required for the diagnosis of colorectal cancer, the method including: measuring the level of STAT3 phosphorylation in Th cells contained in a first sample; and measuring the level of STAT3 phosphorylation in Tc cells contained in a second sample.

DETAILED DESCRIPTION

Hereinafter, the present disclosure will be described in more detail by the following examples. However, these examples are used only for illustration, and the scope of the present disclosure is not limited by these examples.

Experimental Example 1: Subject Collection

The subject group included a colorectal cancer group and a healthy group. The colorectal cancer group was composed of patients before surgery and anticancer treatment among patients diagnosed with colorectal cancer in a biopsy during colonoscopy. About 10 ml of fresh peripheral blood was collected prior to surgery, from each of the patients who verbally consented, into a test tube containing heparin as an anti-coagulant. The blood from healthy persons was obtained from an external tissue bank (Korea Gynecology Cancer Back). The blood was promptly delivered to a laboratory of our center on the day of collection.

Experimental Example 2: Cell Isolation, Stimulation, and Fixation

Mononuclear were isolated from fresh whole blood by using a specific gravity liquid (1.077) such as Ficoll. The isolation method followed a typical method. Briefly, whole blood was diluted with RPMI1640 medium at 1:1, and then Ficoll and the diluted whole blood were placed in a 50-ml test tube at a ratio of 1:1. After centrifugation at 1300 rpm (350 g) for 20 minutes, the mononuclear cell layer separated between Ficoll and plasma was carefully recovered. The isolated mononuclear cells were suspended in RPMI 1640 culture medium containing 10% fetal bovine serum (FBS), at a concentration of $0.5 \times 10^6$ to $1.0 \times 10^6$ cells/ml, and then 1.0 ml was dispensed in each of test tubes prepared under the conditions of test tubes 1 to 4 (test tube 1: no cytokine 1 stimulation (unstimulated, unstim), test tube 2: cytokine 1 stimulated (stimulated, stim), test tube 3: no cytokine 2 stimulation (unstimulated, unstim), and test tube 4: cytokine 2 stimulation (stimulated, stim), and the like) according to the number of cytokines to be identified, and corresponding cytokines were added thereto according to Table 1 below, followed by incubation in a 37° C. incubator for 15 minutes. When the phosphorylated STAT protein (pSTAT) targets to be measured are the same, even different cytokines may share the unstim test tubes. The optimal concentration for each cytokine is shown in Table 1 below. The optimal concentration and reaction time were established through prior experiments.

Then, the test tubes were taken out, and quickly treated with 1.5% paraformaldehyde, and then left at room temperature at 25° C. for 10 minutes, and the supernatant was removed by centrifugation at 1000 rpm (300 g) for 10 minutes. Then, the cells were well suspended as single cells by using a mixer (vortex), and 1.0 ml of a cold 100% methanol stock solution, which had been stored at −20° C. or lower, was added to fix the cells. Care is taken to ensure that the cells were sufficiently present as single cells by adding the cells while mixing cells on the mixer, even during addition. Then, the cells were fixed in a −70° C. refrigerator for 1 hour or longer.

TABLE 1

| | Cytokine | | |
|---|---|---|---|
| | IL-6 | IL-10 | IL-2 |
| Concentration | 20 ng/ml | 10 ng/ml | 20 ng/ml |

Experimental Example 3: Phosphorylation Staining and Flow Cytometry

The upper methanol was removed by centrifugation at 1000 rpm (300 g) for 10 minutes, and then the cells were washed three times with phosphate buffered saline (PBS) containing 0.5% bovine serum albumin (BSA) to completely remove the residual liquid. A monoclonal antibody to pSTAT to be identified and a monoclonal antibody cocktail capable of identifying cell fraction were prepared, and then mixed and incubated with the cell suspension to make a final volume of 100 μl. The cells were incubated in a dark place for 30 minutes, washed once with PBS containing 0.5% BSA, and then re-suspended in 300 μl, and thereafter, subjected to acquisition and analysis by using a flow cytometer.

The composition of each test tube for cytokine stimulation is shown in Table 2, and the composition of the antibody reagent used for each test tube is shown in Table 3.

In addition, helper T cells and cytotoxic T cells were discriminated by a particular monoclonal marker, and then the median value (median MFI) of the pSTAT expression levels (mean fluorescence intensity, MFI) to each cytokine stimulation on histogram was derived under unstim and stim conditions. Finally, the ratio of stim MFI/unstim MFI was expressed and the results are shown in Table 4.

TABLE 2

| | Test tube | | | | | |
|---|---|---|---|---|---|---|
| | 1 | 2 | 3 | 4 | 5 | 6 |
| Stimulant | None | None | IL-6 | IL-6 | IL-10 | IL-2 |
| Concentration | — | — | 20 ng/ml | 20 ng/ml | 10 ng/ml | 20 ng/ml |

TABLE 3

| Stain antibody/Test tube | 1 | 2 | 3 | 4 | 5 | 6 |
|---|---|---|---|---|---|---|
| pSTAT1 (FITC) | 5 | — | 5 | — | — | — |
| pSTAT3 (FITC) | — | 5 | — | 5 | 5 | — |
| pSTAT3 (FITC)5 | — | — | — | — | — | 5 |
| CD25 (PE) | 2 | 2 | 2 | 2 | 2 | 2 |
| CD3 (PercpCY5.5) | 10 | 10 | 10 | 10 | 10 | 10 |
| CD4 (PE-CY7) | 5 | 5 | 5 | 5 | 5 | 5 |
| CD45(APC-CY7) | 5 | 5 | 5 | 5 | 5 | 5 |

Example 1: Levels of STAT Phosphorylation to Cytokines in Immune Cells

The levels of phosphorylated STAT proteins (pSTAT) in response to IL-6, IL-10 and IL-2 in the immune cells of the peripheral blood and tumor tissue of the patients and the peripheral blood of the healthy control were observed, and the results are shown in FIGS. 1 to 5 and Tables 4 to 7 (peripheral blood) and Tables 8 to 11 (tumor site).

TABLE 4

| ID\CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_01 | NA | 2.79 | 1.67 | 0.95 | NA | 2.24 |
| CRC_CIPS_02 | NA | 1.96 | 3.35 | 1.92 | NA | 2.04 |
| CRC_CIPS_03 | NA | 6.59 | 3.46 | 2.8 | NA | 3.94 |
| CRC_CIPS_04 | NA | 16.9 | 3.53 | 3.3 | NA | 7.19 |
| CRC_CIPS_05 | NA | 9.68 | 4.1 | 4.03 | NA | 5.48 |
| CRC_CIPS_06 | NA | 15.7 | 3.53 | 3.14 | NA | 5.51 |
| CRC_CIPS_07 | NA | 7.09 | 4.07 | 3.37 | NA | 2.85 |
| CRC_CIPS_08 | NA | 6.75 | 4.66 | 5.46 | NA | 3.79 |
| CRC_CIPS_09 | NA | 14.4 | 7.66 | 8.34 | NA | 7.99 |
| CRC_CIPS_10 | NA | 14 | 7.81 | 9.04 | NA | 7.67 |
| CRC_CIPS_11 | NA | 1.59 | 3.88 | 3.81 | NA | 1.68 |
| CRC_CIPS_12 | NA | 3 | 4.4 | 3.41 | NA | 1.83 |
| CRC_CIPS_13 | NA | 8.23 | 2.86 | 1.46 | NA | 3.1 |
| CRC_CIPS_14 | NA | 8.15 | 6.83 | 2.55 | NA | 4.68 |
| CRC_CIPS_15 | NA | 3.75 | 5.26 | 3 | NA | 2.04 |

| ID\CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_01 | 1.57 | 1.22 | NA | 2.52 | 1.68 | 0.95 |
| CRC_CIPS_02 | 3.53 | 2.34 | NA | 0.89 | 1.3 | 2.27 |
| CRC_CIPS_03 | 3.56 | 3.43 | NA | 0.89 | 0.92 | 3.47 |

TABLE 4-continued

| | | | | | | |
|---|---|---|---|---|---|---|
| CRC_CIPS_04 | 4.05 | 4.38 | NA | 1 | 1.11 | 5.91 |
| CRC_CIPS_05 | 4.79 | 5.55 | NA | 1.04 | 1.26 | 7.9 |
| CRC_CIPS_06 | 3.28 | 3.85 | NA | 1.48 | 1.23 | 4.66 |
| CRC_CIPS_07 | 4.11 | 4.03 | NA | 1.08 | 1.14 | 5.21 |
| CRC_CIPS_08 | 4.43 | 5.14 | NA | 1.37 | 1.48 | 6.9 |
| CRC_CIPS_09 | 6.59 | 7.47 | NA | 1.3 | 1.57 | 9.87 |
| CRC_CIPS_10 | 6.94 | 7.91 | NA | 1.33 | 1.24 | 9.86 |
| CRC_CIPS_11 | 3.24 | 3.6 | NA | 1.14 | 1.38 | 4.4 |
| CRC_CIPS_12 | 4.26 | 4.34 | NA | 1.08 | 1.59 | 5.89 |
| CRC_CIPS_13 | 3.93 | 1.95 | NA | 1.6 | 1.3 | 1.86 |
| CRC_CIPS_14 | 6.71 | 3.84 | NA | 0.97 | 1.14 | 3.81 |
| CRC_CIPS_15 | 4.57 | 3.98 | NA | 1.64 | 1.14 | 4 |

TABLE 5

| ID\CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_16 | NA | 0.84 | 1.22 | 6.97 | NA | 2.75 |
| CRC_CIPS_17 | NA | 2.13 | 4.11 | 3.27 | NA | 2.09 |
| CRC_CIPS_18 | NA | 5 | 8.99 | 4.19 | NA | 2.49 |
| CRC_CIPS_19 | NA | 5.13 | 5.04 | 3.55 | NA | 4.52 |
| CRC_CIPS_20 | NA | 2.4 | 6.09 | 3.24 | NA | 2.92 |
| CRC_CIPS_21 | NA | 9.71 | 4.11 | 2.71 | NA | 17.6 |
| CRC_CIPS_22 | NA | 7.07 | 1.53 | 1.14 | NA | 4.64 |
| CRC_CIPS_23 | NA | 4.61 | 3.73 | 1.57 | NA | 7.29 |
| CRC_CIPS_24 | NA | 13.2 | 6.06 | 3.97 | NA | 9.5 |
| CRC_CIPS_25 | 5.67 | NA | 5.57 | 4.3 | 12.6 | NA |
| CRC_CIPS_26 | 3.6 | 5.49 | 5.21 | 3.75 | 6.3 | 3.84 |
| CRC_CIPS_27 | 3.08 | 7.34 | 3.36 | 1.75 | 6.53 | 6.11 |
| CRC_CIPS_28 | 3.97 | 9.2 | 5.56 | 5.42 | 5.93 | 10 |
| CRC_CIPS_29 | NA | NA | 6.04 | 5.35 | NA | NA |
| CRC_CIPS_30 | 3.18 | 2.19 | 4.39 | 3.61 | 5.44 | 2.38 |

| ID\CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_16 | 8.7 | 6.59 | NA | 0.82 | 1.16 | 7.4 |
| CRC_CIPS_17 | 4.42 | 3.81 | NA | 0.97 | 1.22 | 3.8 |
| CRC_CIPS_18 | 11.7 | 7.03 | NA | 1.08 | 1.49 | 5.52 |
| CRC_CIPS_19 | 6.08 | 5.01 | NA | 1.16 | 1.27 | 7.24 |
| CRC_CIPS_20 | 7 | 4.09 | NA | 1.23 | 1.14 | 4.6 |
| CRC_CIPS_21 | 8.53 | 6.33 | NA | 1.02 | 1.25 | 7.21 |
| CRC_CIPS_22 | 1.02 | 1.29 | NA | 1.1 | 0.31 | 1.25 |
| CRC_CIPS_23 | 4.46 | 2.04 | NA | 1.29 | 1.09 | 1.83 |
| CRC_CIPS_24 | 9.11 | 6.95 | NA | 1.12 | 1.47 | 3.97 |
| CRC_CIPS_25 | 10.4 | 9.59 | 7.16 | NA | 1.19 | 6.65 |
| CRC_CIPS_26 | 10.5 | 10.8 | 4.64 | 1.33 | 1.22 | 5.07 |
| CRC_CIPS_27 | 3.07 | 2.27 | 2.38 | 1.25 | 1.02 | 1.78 |
| CRC_CIPS_28 | 5.49 | 6.47 | 3.79 | 1.05 | 1.15 | 5.38 |
| CRC_CIPS_29 | 5.69 | 6.02 | NA | NA | 1.42 | 6.02 |
| CRC_CIPS_30 | 4.83 | 4.74 | 2.58 | 1.14 | 1.4 | 3.56 |

TABLE 6

| ID\CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_31 | 3.67 | NA | 5.42 | NA | 7.14 | NA |
| CRC_CIPS_32 | 3.36 | NA | 5.57 | NA | 6.04 | NA |
| CRC_CIPS_33 | 3.27 | NA | 4.57 | NA | 5.06 | NA |
| CRC_CIPS_34 | 3.26 | NA | 3 | NA | 5.03 | NA |
| CRC_CIPS_35 | 3.73 | 7.46 | 6.41 | 1.5 | 7.96 | 2.04 |
| CRC_CIPS_36 | 2.96 | 11.1 | 5.82 | 2.7 | 5.96 | 15.1 |
| CRC_CIPS_37 | 5.63 | NA | 5.4 | 2.25 | 7.48 | NA |
| CRC_CIPS_38 | 6.19 | NA | 4.74 | 4.15 | 13.8 | NA |
| CRC_CIPS_39 | 5.09 | NA | 3.65 | 2.98 | 7.18 | NA |
| CRC_CIPS_40 | 3.96 | NA | 3.72 | 1.72 | 6.8 | NA |

| ID\CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_31 | 4.98 | NA | 3.32 | NA | 1.04 | NA |
| CRC_CIPS_32 | 7.2 | NA | 3.37 | NA | 1.25 | NA |
| CRC_CIPS_33 | 5.73 | NA | 3.19 | NA | 1.16 | NA |

TABLE 6-continued

| | | | | | | |
|---|---|---|---|---|---|---|
| CRC_CIPS_34 | 4.03 | NA | 2.53 | NA | 1.12 | NA |
| CRC_CIPS_35 | 5.05 | 1.93 | 4.13 | 1.08 | 1.26 | 1.65 |
| CRC_CIPS_36 | 5.94 | 3.91 | 4 | 1.12 | 1.17 | 2.83 |
| CRC_CIPS_37 | 6.59 | 3.81 | 4.55 | NA | 1.09 | 2.24 |
| CRC_CIPS_38 | 7.48 | 7.14 | 5.19 | NA | 1.28 | 4.38 |
| CRC_CIPS_39 | 4.18 | 4.02 | 4.43 | NA | 1.18 | 3.27 |
| CRC_CIPS_40 | 4.76 | 2.62 | 2.8 | NA | 0.95 | 1.53 |

TABLE 7

| ID\CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CON_CIPS_01 | 3.7 | 9.48 | 4.93 | 2.27 | 6.67 | 6.75 |
| CON_CIPS_02 | 3.13 | 7.39 | 4.54 | 2.15 | 8.86 | 7.39 |
| CON_CIPS_03 | 4.76 | 15.4 | 4.67 | 2.38 | 12.1 | 13.4 |
| CON_CIPS_04 | 5.22 | 16 | 2.71 | 1.54 | 12 | 19.4 |
| CON_CIPS_05 | 3.57 | 15 | 3.41 | 1.68 | 6.85 | 12.9 |
| CON_CIPS_06 | 2.73 | 13.3 | 4.63 | 2.06 | 5.56 | 6.72 |
| CON_CIPS_07 | 2.77 | 7.91 | 4.13 | 2.06 | 5.79 | 4.61 |
| CON_CIPS_08 | 2.31 | 9.55 | 3.55 | 2 | 4.63 | 7.9 |
| CON_CIPS_09 | 8.92 | 5.95 | 5.35 | 2.91 | 23.8 | 4.88 |
| CON_CIPS_10 | 9.88 | 3.46 | 6.47 | 2.49 | 22 | 3.97 |
| CON_CIPS_11 | 7.47 | 3.16 | 4.93 | 2.76 | 19.6 | 4.55 |
| CON_CIPS_12 | 3.42 | 8.27 | 3.05 | 1.63 | 4.99 | 6.89 |
| CON_CIPS_13 | 2.77 | 10.5 | 3.13 | 1.83 | 4.21 | 9.75 |
| CON_CIPS_14 | 2.3 | 10.3 | 4.09 | 2.17 | 4.65 | 9.03 |
| CON_CIPS_15 | 3.91 | 9.11 | 4.92 | 1.49 | 10.9 | 5.66 |
| CON_CIPS_16 | 4.86 | 15.4 | 4.06 | 1.49 | 10.4 | 8.41 |

| ID\CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CON_CIPS_01 | 5.43 | 3.8 | 2.42 | 7.69 | 3.85 | 2.22 |
| CON_CIPS_02 | 5.15 | 3.42 | 2.98 | 1.17 | 1.36 | 2.62 |
| CON_CIPS_03 | 6 | 4.14 | 6.17 | 1.71 | 1.8 | 3.25 |
| CON_CIPS_04 | 3.55 | 2.45 | 5.55 | 15.5 | 2.67 | 1.83 |
| CON_CIPS_05 | 3.57 | 2.46 | 3.46 | 2.92 | 2.33 | 1.75 |
| CON_CIPS_06 | 4.46 | 3.06 | 2.87 | 1.34 | 1.48 | 2.61 |
| CON_CIPS_07 | 4.26 | 2.92 | 2.45 | 1.63 | 1.91 | 2.21 |
| CON_CIPS_08 | 4.07 | 2.78 | 1.92 | 2.88 | 2.17 | 1.95 |
| CON_CIPS_09 | 10.3 | 8.5 | 8.67 | 1.4 | 1.33 | 4.14 |
| CON_CIPS_10 | 8.91 | 5.3 | 7.39 | 0.92 | 1.07 | 3.3 |
| CON_CIPS_11 | 6.25 | 4.72 | 4.99 | 1.1 | 1.28 | 3.36 |
| CON_CIPS_12 | 2.84 | 1.84 | 2.93 | 1.53 | 1.39 | 1.68 |
| CON_CIPS_13 | 2.68 | 2.14 | 3.19 | 1.33 | 1.42 | 2.03 |
| CON_CIPS_14 | 3.72 | 2.67 | 2.78 | 1.53 | 1.59 | 2.36 |
| CON_CIPS_15 | 5.17 | 2.23 | 3.29 | 1.67 | 1.74 | 1.75 |
| CON_CIPS_16 | 4.04 | 2.4 | 4.51 | 2.4 | 2.32 | 1.54 |

TABLE 8

| ID/CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_01 | NA | 1 | 0.72 | NA | NA | 1.25 |
| CRC_CIPS_02 | NA | 2.05 | 1.77 | 1.39 | NA | 2.2 |
| CRC_CIPS_03 | NA | 1.56 | 1.98 | 1.09 | NA | 1.48 |
| CRC_CIPS_04 | NA | 1.34 | 1.16 | 1.51 | NA | 1.49 |
| CRC_CIPS_05 | NA | 1.01 | 0.84 | 1.61 | NA | 1.11 |
| CRC_CIPS_06 | NA | 1.35 | 0.91 | 2.28 | NA | 1.67 |
| CRC_CIPS_07 | NA | 1.03 | 1.2 | 2.02 | NA | 1.15 |
| CRC_CIPS_08 | NA | 1.6 | 1.46 | 3.37 | NA | 1.8 |
| CRC_CIPS_09 | NA | 0.94 | 1.13 | 2.42 | NA | 0.84 |
| CRC_CIPS_10 | NA | 0.94 | 1.3 | 2.58 | NA | 1 |
| CRC_CIPS_11 | NA | 1.12 | 1.26 | 1.46 | NA | 1.1 |
| CRC_CIPS_12 | NA | 1.04 | 1.14 | 2.01 | NA | 1.08 |
| CRC_CIPS_13 | NA | 0.59 | 1.18 | 1.37 | NA | 0.59 |
| CRC_CIPS_14 | NA | 1.13 | 1.92 | 2.01 | NA | 1.45 |
| CRC_CIPS_15 | NA | 1.24 | 1.01 | 2 | NA | 1.17 |

TABLE 8-continued

| ID/CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_01 | 0.65 | | NA | 0.97 | 0.87 | |
| CRC_CIPS_02 | 1.7 | 1.48 | NA | 1.29 | 1.13 | 1.48 |
| CRC_CIPS_03 | 2.06 | 1.14 | NA | 0.94 | 1.26 | 1.17 |
| CRC_CIPS_04 | 1.47 | 1.61 | NA | 1.04 | 0.97 | 1.78 |
| CRC_CIPS_05 | 0.96 | 2.04 | NA | 1.05 | 0.93 | 2.16 |
| CRC_CIPS_06 | 1.44 | 3 | NA | 1.23 | 1.06 | 4.3 |
| CRC_CIPS_07 | 1.27 | 2.37 | NA | 1.02 | 1.03 | 2.43 |
| CRC_CIPS_08 | 1.7 | 3.5 | NA | 1.11 | 1.27 | 6.12 |
| CRC_CIPS_09 | 0.96 | 2.22 | NA | 1.06 | 1.01 | 3.49 |
| CRC_CIPS_10 | 1.38 | 2.75 | NA | 0.85 | 1.23 | 4.65 |
| CRC_CIPS_11 | 1.46 | 0.55 | NA | 1.42 | 1.46 | 3.43 |
| CRC_CIPS_12 | 1.14 | 2.13 | NA | 1.42 | 1.01 | 2.07 |
| CRC_CIPS_13 | 1.46 | 1.55 | NA | 0.48 | 0.98 | 1.49 |
| CRC_CIPS_14 | 2.91 | 3.1 | NA | 0.8 | 1.12 | 2.22 |
| CRC_CIPS_15 | 1.34 | 2.56 | NA | 1.12 | 1.07 | 2.85 |

TABLE 9

| ID/CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_16 | NA | 1.85 | 2.41 | 1.9 | NA | 2.45 |
| CRC_CIPS_17 | NA | 0.89 | 1.12 | 1.52 | NA | 0.92 |
| CRC_CIPS_18 | NA | 0.94 | 1.46 | 2.28 | NA | 0.82 |
| CRC_CIPS_19 | NA | 0.99 | 1.26 | 2.33 | NA | 1.28 |
| CRC_CIPS_20 | NA | 1.73 | 3.32 | 1.87 | NA | 3.22 |
| CRC_CIPS_21 | NA | 1.39 | 1.81 | 2.2 | NA | 8.27 |
| CRC_CIPS_22 | NA | 1.65 | 2.32 | 1.93 | NA | 2.24 |
| CRC_CIPS_23 | NA | 0.94 | 1.06 | 3.72 | NA | 2 |
| CRC_CIPS_24 | NA | 1.53 | 1.73 | 2.35 | NA | 1.68 |
| CRC_CIPS_25 | 3.33 | NA | 1.86 | 1.68 | 12.7 | NA |
| CRC_CIPS_26 | 3.79 | 1.39 | 1.42 | 2.53 | 9.69 | 1.71 |
| CRC_CIPS_27 | 3 | 1.05 | 1.26 | 1.4 | 5.93 | 1.04 |
| CRC_CIPS_28 | 2.84 | 1.2 | 1.2 | 2.8 | 5.21 | 2.23 |
| CRC_CIPS_29 | 4.43 | 1.17 | 1.15 | 1.95 | 6.08 | 1.96 |
| CRC_CIPS_30 | 2.53 | NA | NA | NA | 4.52 | NA |

| ID/CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_16 | 3.05 | 2.6 | NA | 1.08 | 1.05 | 2.66 |
| CRC_CIPS_17 | 1.37 | 2.04 | NA | 0.77 | 0.92 | 1.4 |
| CRC_CIPS_18 | 1.49 | 2.92 | NA | 0.89 | 1.25 | 2.78 |
| CRC_CIPS_19 | 2.12 | 4.12 | NA | 0.89 | 1.08 | 2.19 |
| CRC_CIPS_20 | 4.96 | 2.6 | NA | 1.08 | 1.21 | 1.87 |
| CRC_CIPS_21 | 8.36 | 7.86 | NA | 1.1 | 1.22 | 3.74 |
| CRC_CIPS_22 | 3 | 3.22 | NA | 0.7 | 0.98 | 1.9 |
| CRC_CIPS_23 | 0.93 | 7.33 | NA | 1 | 1.11 | 4.56 |
| CRC_CIPS_24 | 2.58 | 3.96 | NA | 1.21 | 1.2 | 2.34 |
| CRC_CIPS_25 | 4.61 | 5.56 | 4.69 | NA | 1.12 | 2.27 |
| CRC_CIPS_26 | 4.89 | 10.6 | 4.08 | 1.07 | 1.06 | 3 |
| CRC_CIPS_27 | 1.3 | 1.68 | 2.4 | 0.92 | 1.04 | 1.45 |
| CRC_CIPS_28 | 2.56 | 4.44 | 3.04 | 1.04 | 1.05 | 2.98 |
| CRC_CIPS_29 | 1.78 | 2.54 | 4.71 | 1.12 | 1.13 | 2.57 |
| CRC_CIPS_30 | NA | NA | 2.3 | NA | NA | NA |

TABLE 10

| ID/CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CRC_CIPS_31 | 2.1 | NA | 1.06 | NA | 4.93 | NA |
| CRC_CIPS_32 | 2.89 | NA | 1.08 | NA | 6.79 | NA |
| CRC_CIPS_33 | 3.04 | NA | 1.06 | NA | 9.39 | NA |
| CRC_CIPS_34 | 3.1 | NA | NA | NA | 8.61 | NA |
| CRC_CIPS_35 | 1.28 | NA | NA | NA | 1.89 | NA |
| CRC_CIPS_36 | 2.35 | NA | 1.21 | 1.05 | 4.21 | NA |
| CRC_CIPS_37 | 3.57 | NA | 1.22 | 1.62 | 7.72 | NA |

TABLE 10-continued

| | | | | | | |
|---|---|---|---|---|---|---|
| CRC_CIPS_38 | 1.85 | NA | 1.32 | 1.34 | 7.82 | NA |
| CRC_CIPS_39 | 1.86 | NA | 1.17 | 1.27 | 4.45 | NA |
| CRC_CIPS_40 | 2.97 | 0.99 | 1.15 | 1.31 | 6.14 | 1.41 |

| ID/CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CRC_CIPS_31 | 2.1 | NA | 2.66 | NA | 0.92 | NA |
| CRC_CIPS_32 | 1.28 | NA | 3.07 | NA | 1.09 | NA |
| CRC_CIPS_33 | 1.1 | NA | 2.62 | NA | 1.09 | NA |
| CRC_CIPS_34 | NA | NA | 2.59 | NA | NA | NA |
| CRC_CIPS_35 | NA | NA | 1.34 | NA | NA | NA |
| CRC_CIPS_36 | 1.71 | NA | 2.04 | NA | 1.11 | 1.15 |
| CRC_CIPS_37 | 1.68 | 2.53 | 3.02 | NA | 1.13 | 1.61 |
| CRC_CIPS_38 | 2.11 | 2.32 | 1.84 | NA | 1.38 | 1.49 |
| CRC_CIPS_39 | 1.2 | 1.65 | 2.08 | NA | 1.09 | 1.38 |
| CRC_CIPS_40 | 1.67 | 1.49 | 3.14 | 1.01 | 1.08 | 1.26 |

TABLE 11

| ID/CIPS | IL-2_pSTAT5_Th | IL-6_pSTAT1_Th | IL-6_pSTAT3_Th | IL-10_pSTAT3_Th | IL-2_pSTAT5_Treg | IL-6_pSTAT1_Treg |
|---|---|---|---|---|---|---|
| CON_CIPS_01 | NA | NA | NA | NA | NA | NA |
| CON_CIPS_02 | NA | NA | NA | NA | NA | NA |
| CON_CIPS_03 | NA | NA | NA | NA | NA | NA |
| CON_CIPS_04 | NA | NA | NA | NA | NA | NA |
| CON_CIPS_05 | NA | NA | NA | NA | NA | NA |
| CON_CIPS_06 | NA | NA | NA | NA | NA | NA |
| CON_CIPS_07 | NA | NA | NA | NA | NA | NA |
| CON_CIPS_08 | NA | NA | NA | NA | NA | NA |
| CON_CIPS_09 | NA | NA | NA | NA | NA | NA |
| CON_CIPS_10 | NA | NA | NA | NA | NA | NA |
| CON_CIPS_11 | NA | NA | NA | NA | NA | NA |
| CON_CIPS_12 | NA | NA | NA | NA | NA | NA |
| CON_CIPS_13 | NA | NA | NA | NA | NA | NA |
| CON_CIPS_14 | NA | NA | NA | NA | NA | NA |
| CON_CIPS_15 | NA | NA | NA | NA | NA | NA |
| CON_CIPS_16 | NA | NA | NA | NA | NA | NA |

| ID/CIPS | IL-6_pSTAT3_Treg | IL-10_pSTAT3_Treg | IL-2_pSTAT5_Tc | IL-6_pSTAT1_Tc | IL-6_pSTAT3_Tc | IL-10_pSTAT3_Tc |
|---|---|---|---|---|---|---|
| CON_CIPS_01 | NA | NA | NA | NA | NA | NA |
| CON_CIPS_02 | NA | NA | NA | NA | NA | NA |
| CON_CIPS_03 | NA | NA | NA | NA | NA | NA |
| CON_CIPS_04 | NA | NA | NA | NA | NA | NA |
| CON_CIPS_05 | NA | NA | NA | NA | NA | NA |
| CON_CIPS_06 | NA | NA | NA | NA | NA | NA |
| CON_CIPS_07 | NA | NA | NA | NA | NA | NA |
| CON_CIPS_08 | NA | NA | NA | NA | NA | NA |
| CON_CIPS_09 | NA | NA | NA | NA | NA | NA |
| CON_CIPS_10 | NA | NA | NA | NA | NA | NA |
| CON_CIPS_11 | NA | NA | NA | NA | NA | NA |
| CON_CIPS_12 | NA | NA | NA | NA | NA | NA |
| CON_CIPS_13 | NA | NA | NA | NA | NA | NA |
| CON_CIPS_14 | NA | NA | NA | NA | NA | NA |
| CON_CIPS_15 | NA | NA | NA | NA | NA | NA |
| CON_CIPS_16 | NA | NA | NA | NA | NA | NA |

As can be seen in FIGS. 1 to 5 and Tables 4 to 11, IL-6-induced pSTAT1 and pSTAT3 were significantly decreased in tumor infiltrating lymphocytes (TILs). It was also identified that the cytokine-induced phosphorylated STAT signature (CIPS signature) of the peripheral blood lymphocytes reflected the CIPS signature of TILs.

Such similar phenomenon was observed in IL-6-induced pSTAT1 of Helper T cells, regulatory T cells, and cytotoxic T cells, as well as in pSTAT3 of Tc cells. However, unusually, IL-10-induced pSTAT3 was similar in both TILs and healthy control cells, but significantly increased in the peripheral blood lymphocytes of the patients.

Overall, it was identified that the levels of intracellular STAT protein phosphorylation (pSTAT) by IL-6 and IL-10 were statistically very different between the immune cells derived from tumor tissue of colorectal cancer patients and the immune cells derived from the blood of normal persons and that there was phosphorylation at the medium levels therebetween in the immune cells derived from the blood of the colorectal cancer patients.

Example 2: In-Vitro Co-Culture Experiment Using Cancer Cell Lines

Figure 6:
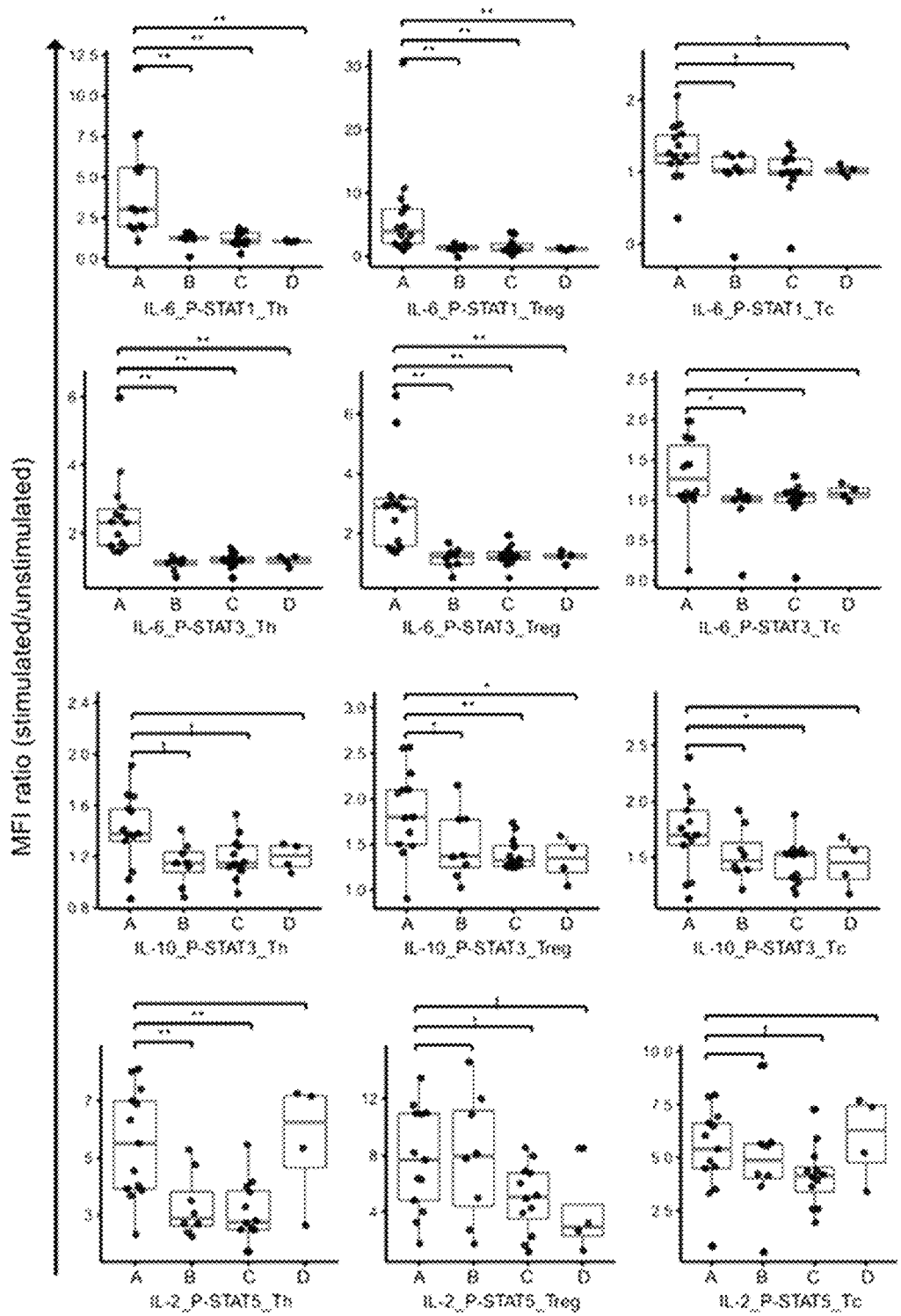
FIG. 6 shows the results of experimenting the change of phosphorylation of each STAT to each cytokine after co-culture of blood immune cells of healthy persons and a colorectal cell line at various ratios according to an embodiment of the present disclosure. On the whole, statistically significant decrease patterns were shown in the immune cells (B, C, and D) co-cultured with the colorectal cell line compared with the base values (A). (A: PBMC only, B: direct culture of PBMC+HCT116 (1:1), C: direct culture of PBMC+HCT116 (1:10), D: indirect culture of PBMC+HCT116 (1:10))

In order to investigate whether the findings observed in the patient-derived immune cells were caused by tumor cells, HCT116 (American Type Culture Collection, ATCC CCL-247), which is a colorectal cancer cell line, and mononuclear cells of the peripheral blood of normal persons were co-cultured in vitro. The cell mixing conditions and the number of cells in the in-vitro co-culture experiment are shown in Table 12. The levels of STAT protein phosphorylation for each cytokine were measured, the results are shown in FIG. 6 and Tables 13 to 15. (Table 13: Th, Table 14: Treg, and Table 15: Tc)

Co-culturing was performed under two conditions. That is, while the ratios of tumor cells and mononuclear cells of normal persons were 1:1 and 1:10, the first condition was that the two kinds of cells were directly mixed and co-cultured in one experimental well (direct), and the second condition was that, in an experimental well with a septum (transwell), the tumor cells were placed in the upper layer of the septum and the mononuclear cells of normal persons were placed in the lower layer and co-cultured (indirect).

TABLE 12

| Ratio | Number of tumor cells | Number of mononuclear cells of normal persons |
|---|---|---|
| 1:1 | $3 \times 10^6$ | $3 \times 10^6$ |
| 1:10 | $3 \times 10^5$ | $3 \times 10^6$ |

TABLE 13

| ID/CIPS | IL-2_pSTAT5_Th | IL-6_pSTAT1_Th | IL-6_pSTAT3_Th | IL-10_pSTAT3_Th |
|---|---|---|---|---|
| PBMC_01 |  | 11.72 | 5.98 |  |
| PBMC_02 | 2.31 | 2.94 | 1.96 | 1.02 |
| PBMC_03 | 3.86 | 1.97 | 1.62 | 1.08 |
| PBMC_04 | 3.92 | 1.88 | 1.72 | 0.87 |
| PBMC_05 | 5.51 | 5.62 | 3.07 | 1.55 |
| PBMC_06 | 6.32 | 7.68 | 2.49 | 1.32 |
| PBMC_07 | 6.88 | 2.03 | 2.76 | 1.41 |
| PBMC_08 | 3.68 | 5.31 | 3.80 | 1.91 |
| PBMC_09 | 8.03 | 3.10 | 2.34 | 1.67 |
| PBMC_10 | 7.00 | 1.82 | 1.45 | 1.37 |
| PBMC_11 | 8.11 | 1.05 | 1.58 | 1.38 |
| PBMC_12 | 4.55 | 2.99 | 1.46 | 1.36 |
| PBMC_13 | 4.04 | 5.49 | 2.29 | 1.57 |
| PBMC_14 | 7.41 | 7.54 | 2.55 | 1.68 |
| PBMC_HCT116_R1_Direct_01 | 3.50 | 0.09 | 0.69 | 1.15 |
| PBMC_HCT116_R1_Direct_02 | 2.23 | 1.47 | 1.12 | 1.15 |
| PBMC_HCT116_R1_Direct_03 | 2.69 | 1.17 | 1.20 | 0.95 |
| PBMC_HCT116_R1_Direct_04 | 2.39 | 1.20 | 1.11 | 1.12 |
| PBMC_HCT116_R1_Direct_05 | 2.71 | 1.28 | 1.18 | 1.41 |
| PBMC_HCT116_R1_Direct_06 | 5.29 | 1.26 | 1.24 | 1.28 |
| PBMC_HCT116_R1_Direct_07 | 3.07 | 1.58 | 1.34 | 1.22 |
| PBMC_HCT116_R1_Direct_08 | 4.76 | 1.30 | 0.90 | 0.88 |
| PBMC_HCT116_R10_Direct_01 | 2.80 | 0.27 | 0.68 | 0.91 |
| PBMC_HCT116_R10_Direct_02 | 1.70 | 1.12 | 1.28 | 1.02 |
| PBMC_HCT116_R10_Direct_03 | 2.47 | 1.68 | 1.43 | 1.09 |
| PBMC_HCT116_R10_Direct_04 | 2.53 | 1.90 | 1.56 | 1.22 |
| PBMC_HCT116_R10_Direct_05 | 1.71 | 1.70 | 1.21 | 1.39 |
| PBMC_HCT116_R10_Direct_06 | 4.16 | 1.38 | 1.36 | 1.16 |
| PBMC_HCT116_R10_Direct_07 | 2.49 | 1.55 | 1.16 | 1.30 |
| PBMC_HCT116_R10_Direct_08 | 3.80 | 0.97 | 1.21 | 1.53 |
| PBMC_HCT116_R10_Direct_09 | 5.46 | 1.08 | 1.22 | 1.14 |
| PBMC_HCT116_R10_Direct_10 | 3.29 | 0.87 | 0.99 | 1.28 |
| PBMC_HCT116_R10_Direct_11 | 2.71 | 0.95 | 1.05 | 1.12 |
| PBMC_HCT116_R10_Direct_12 | 4.00 | 0.86 | 1.15 | 1.12 |
| PBMC_HCT116_R10_Indirect_01 | 7.26 | 1.09 | 1.30 | 1.07 |
| PBMC_HCT116_R10_Indirect_02 | 7.16 | 1.14 | 1.30 | 1.28 |
| PBMC_HCT116_R10_Indirect_03 | 2.63 | 1.04 | 0.97 | 1.14 |
| PBMC_HCT116_R10_Indirect_04 | 5.34 | 1.01 | 1.16 | 1.30 |

TABLE 14

| ID/CIPS | IL-2_pSTAT5_Treg | IL-6_pSTAT1_Treg | IL-6_pSTAT3_Treg | IL-10_pSTAT3_Treg |
|---|---|---|---|---|
| PBMC_01 |  | 30.51 | 6.61 |  |
| PBMC_02 | 4.01 | 2.29 | 1.75 | 1.48 |
| PBMC_03 | 3.25 | 1.98 | 5.70 | 2.10 |
| PBMC_04 | 10.92 | 9.03 | 1.43 | 0.90 |
| PBMC_05 | 13.47 | 3.28 | 3.02 | 1.80 |
| PBMC_06 | 10.96 | 10.74 | 3.28 | 2.57 |
| PBMC_07 | 11.54 | 3.29 | 2.44 | 1.79 |
| PBMC_08 | 6.27 | 4.53 | 2.80 | 2.28 |
| PBMC_09 | 7.68 | 4.75 | 3.22 | 2.10 |
| PBMC_10 | 11.00 | 1.63 | 1.35 | 1.41 |

TABLE 14-continued

| ID/CIPS | IL-2_pSTAT5_Treg | IL-6_pSTAT1_Treg | IL-6_pSTAT3_Treg | IL-10_pSTAT3_Treg |
| --- | --- | --- | --- | --- |
| PBMC_11 | 8.19 | 0.97 | 1.52 | 1.63 |
| PBMC_12 | 4.82 | 1.63 | 1.52 | 1.50 |
| PBMC_13 | 1.74 | 6.84 | 2.98 | 2.56 |
| PBMC_14 | 6.36 | 7.70 | 2.94 | 2.06 |
| PBMC_HCT116_R1_Direct_01 | 4.98 | −0.12 | 0.52 | 1.78 |
| PBMC_HCT116_R1_Direct_02 | 2.72 | 1.15 | 1.69 | 1.77 |
| PBMC_HCT116_R1_Direct_03 | 1.73 | 0.96 | 1.45 | 1.28 |
| PBMC_HCT116_R1_Direct_04 | 12.00 | 1.15 | 1.17 | 1.38 |
| PBMC_HCT116_R1_Direct_05 | 10.88 | 2.14 | 1.27 | 2.15 |
| PBMC_HCT116_R1_Direct_06 | 7.77 | 1.72 | 0.98 | 1.15 |
| PBMC_HCT116_R1_Direct_07 | 8.14 | 1.65 | 1.33 | 1.36 |
| PBMC_HCT116_R1_Direct_08 | 14.60 | 1.31 | 0.94 | 1.02 |
| PBMC_HCT116_R10_Direct_01 | 4.94 | 0.11 | 0.51 | 1.47 |
| PBMC_HCT116_R10_Direct_02 | 1.61 | 1.15 | 1.45 | 1.24 |
| PBMC_HCT116_R10_Direct_03 | 1.16 | 2.26 | 1.93 | 1.34 |
| PBMC_HCT116_R10_Direct_04 | 8.56 | 3.58 | 1.62 | 1.26 |
| PBMC_HCT116_R10_Direct_05 | 4.27 | 1.45 | 1.16 | 1.68 |
| PBMC_HCT116_R10_Direct_06 | 6.02 | 3.75 | 1.37 | 1.29 |
| PBMC_HCT116_R10_Direct_07 | 5.20 | 1.89 | 1.27 | 1.74 |
| PBMC_HCT116_R10_Direct_08 | 7.94 | 0.87 | 1.24 | 1.54 |
| PBMC_HCT116_R10_Direct_09 | 6.89 | 0.96 | 0.96 | 1.31 |
| PBMC_HCT116_R10_Direct_10 | 6.72 | 0.80 | 1.21 | 1.37 |
| PBMC_HCT116_R10_Direct_11 | 2.27 | 0.95 | 1.02 | 1.25 |
| PBMC_HCT116_R10_Direct_12 | 3.92 | 1.01 | 1.15 | 1.26 |
| PBMC_HCT116_R10_Indirect_01 | 8.50 | 0.93 | 1.24 | 1.04 |
| PBMC_HCT116_R10_Indirect_02 | 3.20 | 1.36 | 1.42 | 1.59 |
| PBMC_HCT116_R10_Indirect_03 | 1.26 | 1.05 | 0.94 | 1.24 |
| PBMC_HCT116_R10_Indirect_04 | 2.68 | 1.27 | 1.27 | 1.46 |

TABLE 15

| ID/CIPS | IL-2_pSTAT5_Tc | IL-6_pSTAT1_Tc | IL-6_pSTAT3_Tc | IL-10 pSTAT3_Tc |
| --- | --- | --- | --- | --- |
| PBMC_01 |  | 1.63 | 1.76 |  |
| PBMC_02 | 3.32 | 0.36 | 0.12 | 1.25 |
| PBMC_03 | 6.04 | 1.22 | 1.06 | 1.27 |
| PBMC_04 | 0.83 | 1.14 | 1.09 | 1.13 |
| PBMC_05 | 6.93 | 1.37 | 1.44 | 1.65 |
| PBMC_06 | 6.63 | 1.66 | 1.98 | 1.61 |
| PBMC_07 | 7.88 | 0.94 | 1.00 | 1.70 |
| PBMC_08 | 3.51 | 1.48 | 1.78 | 1.92 |
| PBMC_09 | 4.58 | 1.27 | 1.41 | 2.13 |
| PBMC_10 | 6.48 | 1.21 | 1.00 | 1.76 |
| PBMC_11 | 7.95 | 0.95 | 1.11 | 1.70 |
| PBMC_12 | 4.86 | 1.12 | 1.05 | 2.39 |
| PBMC_13 | 4.50 | 2.06 | 1.98 | 1.82 |
| PBMC_14 | 5.40 | 1.53 | 1.44 | 2.00 |
| PBMC_HCT116_R1_Direct_01 | 4.15 | −0.18 | 0.06 | 1.81 |
| PBMC_HCT116_R1_Direct_02 | 4.22 | 1.24 | 1.00 | 1.39 |
| PBMC_HCT116_R1_Direct_03 | 0.55 | 0.98 | 1.05 | 1.42 |
| PBMC_HCT116_R1_Direct_04 | 5.71 | 1.00 | 1.01 | 1.57 |
| PBMC_HCT116_R1_Direct_05 | 5.53 | 1.00 | 1.00 | 1.92 |
| PBMC_HCT116_R1_Direct_06 | 5.64 | 1.07 | 1.04 | 1.52 |
| PBMC_HCT116_R1_Direct_07 | 3.64 | 1.25 | 1.11 | 1.38 |
| PBMC_HCT116_R1_Direct_08 | 9.34 | 1.21 | 0.89 | 1.21 |
| PBMC_HCT116_R10_Direct_01 | 4.06 | −0.06 | 0.03 | 1.52 |
| PBMC_HCT116_R10_Direct_02 | 3.92 | 0.99 | 1.09 | 1.28 |
| PBMC_HCT116_R10_Direct_03 | 1.94 | 1.18 | 1.10 | 1.53 |
| PBMC_HCT116_R10_Direct_04 | 5.05 | 1.19 | 1.29 | 1.54 |
| PBMC_HCT116_R10_Direct_05 | 2.59 | 1.39 | 1.06 | 1.57 |
| PBMC_HCT116_R10_Direct_06 | 4.36 | 1.14 | 0.90 | 1.57 |
| PBMC_HCT116_R10_Direct_07 | 2.56 | 1.30 | 1.16 | 1.53 |
| PBMC_HCT116_R10_Direct_08 | 3.64 | 0.90 | 1.09 | 1.88 |
| PBMC_HCT116_R10_Direct_09 | 5.91 | 1.01 | 1.01 | 1.17 |
| PBMC_HCT116_R10_Direct_10 | 7.27 | 0.79 | 0.96 | 1.35 |
| PBMC_HCT116_R10_Direct_11 | 4.39 | 0.98 | 0.98 | 1.22 |
| PBMC_HCT116_R10_Direct_12 | 4.22 | 1.00 | 1.03 | 1.32 |
| PBMC_HCT116_R10_Indirect_01 | 7.69 | 1.11 | 1.21 | 1.17 |
| PBMC_HCT116_R10_Indirect_02 | 7.38 | 1.00 | 1.13 | 1.68 |
| PBMC_HCT116_R10_Indirect_03 | 3.39 | 1.04 | 0.98 | 1.35 |
| PBMC_HCT116_R10_Indirect_04 | 5.23 | 0.93 | 1.05 | 1.56 |

As can be seen from FIG. 6 and Tables 13 to 15, it was observed that in both cases of direct contact culture or indirect culture with tumor cells, abnormality was induced in cytokine signaling in peripheral lymphocytes of normal persons similar to T cells of the tumor infiltrating environment. In addition, this was not affected by the ratio of normal cells and tumor cell lines in co-culture or the manner of direct or indirect culture (1:1 and 1:10). However, the IL-2-induced pSTAT5 signatures were not observed to show significant decreases in all of Th cells, Tc cells, and Treg cells. Especially, almost similar levels of phosphorylation in Treg cells, suggesting that no functional abnormality occurred in response to IL-2 in the STAT signaling system even in the tumor environment. Overall, similar to the results in actual patients, the levels of pSTAT by IL-6 and IL-10 were statistically significantly different, and mainly decreased in the immune T cells cultured with tumor cells.

Test Example: Cluster Analysis

CIPS signatures of 30 CRC patients and 15 healthy persons were subjected to cluster analysis. Specifically, the distances between sample results were analyzed by the hierarchical clustering method using R language, and in order to schematize the distances, a heatmap was drawn using the gplot R package. The results are shown in FIG. 7.

Figure 7:
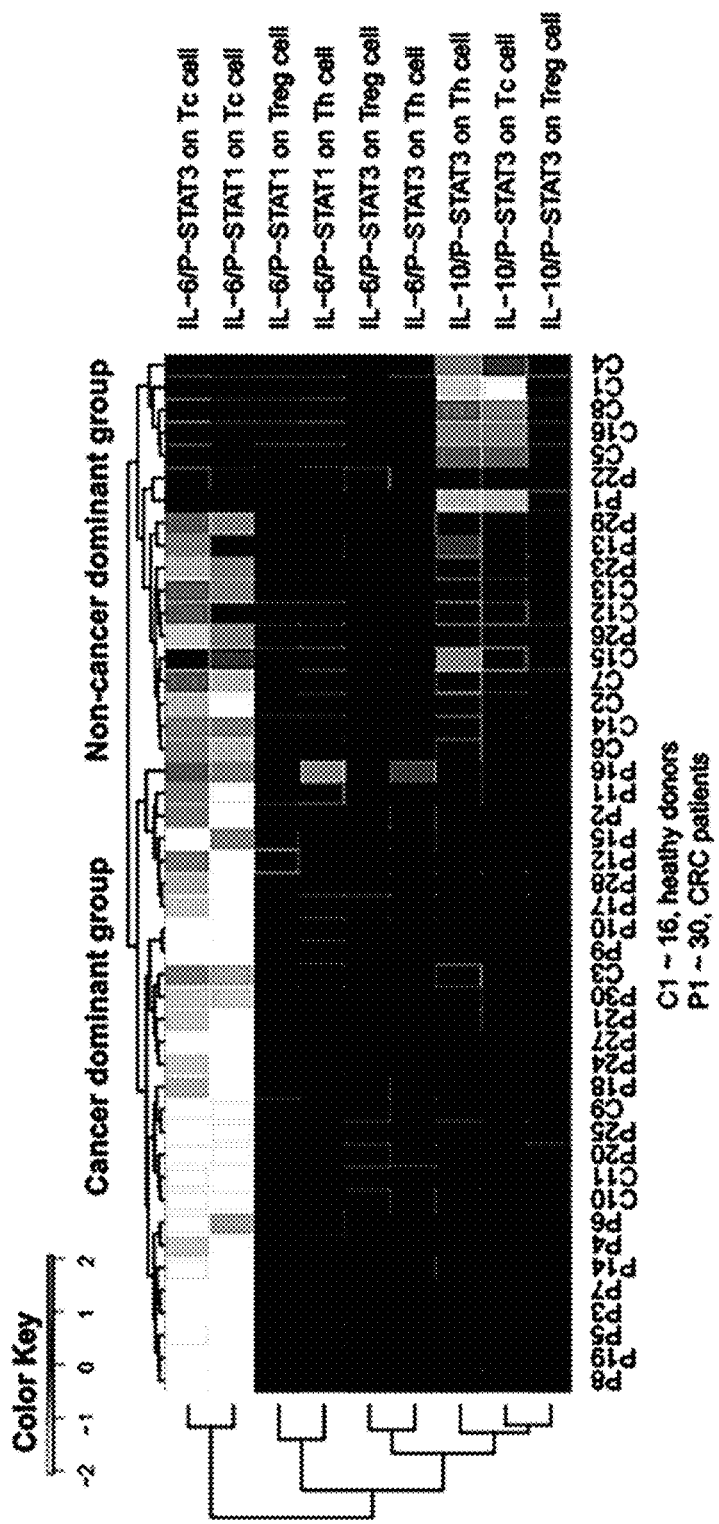
FIG. 7 shows that cluster analysis was performed with the levels of phosphorylation of each STAT to each cytokine according to an embodiment of the present disclosure, and resultantly, there were two groups wherein colorectal patients were mainly distributed in one group and healthy persons were mainly distributed in the other group.

As can be seen in FIG. 7, between the two groups, there were distinct differences in the IL-10-induced pSTAT3 signatures on Th, Treg, and Tc cells.

Test Example: Principal Component Aanalysis

Figure 8:
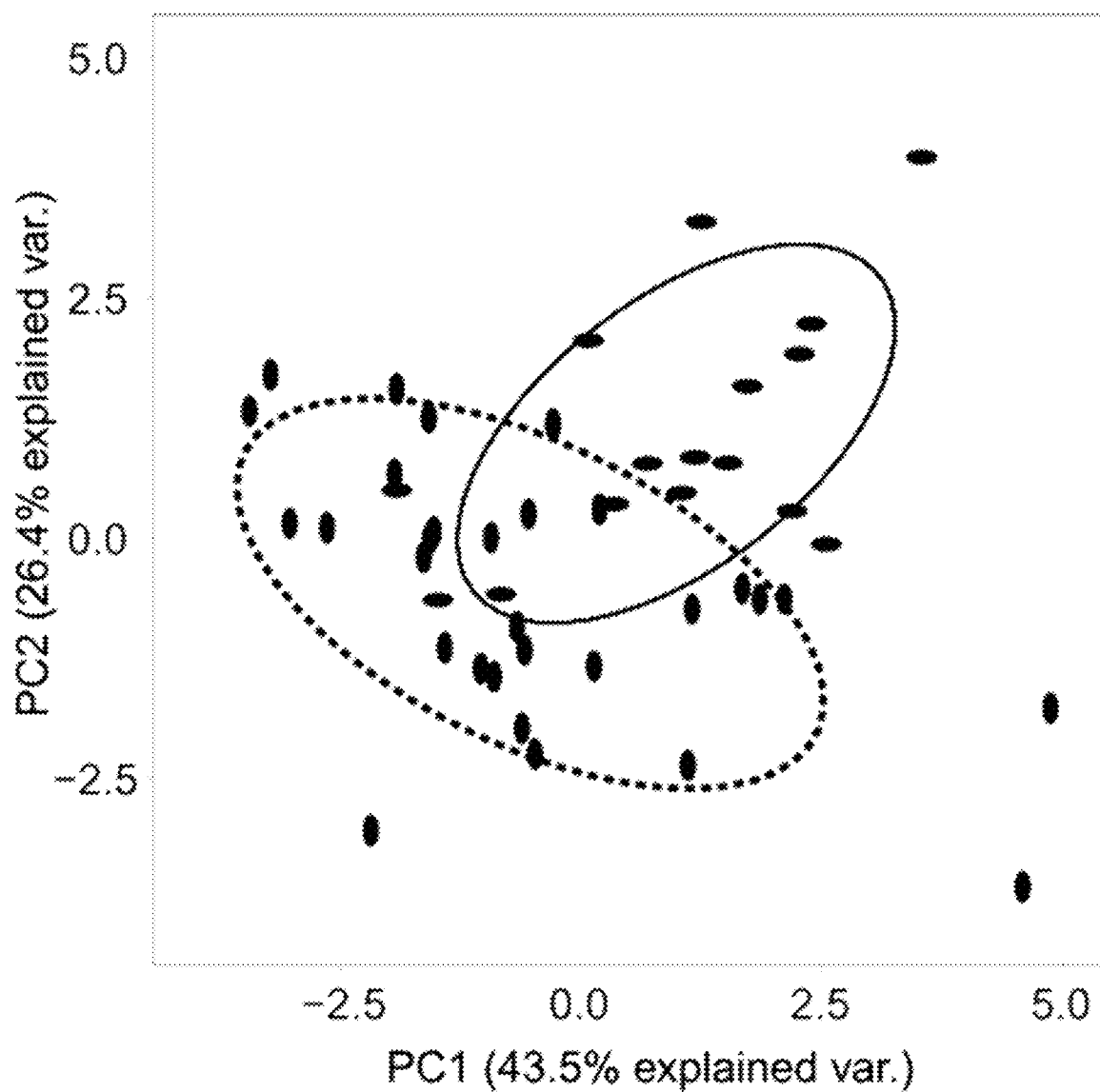
FIG. 8 shows that principal component analysis (PCA) was performed with the phosphorylation levels of each STAT to each cytokine according to an embodiment of the present disclosure and that the colorectal cancer patients (red dots) and healthy persons (green dots) were discriminated from each other.
Figure 9:
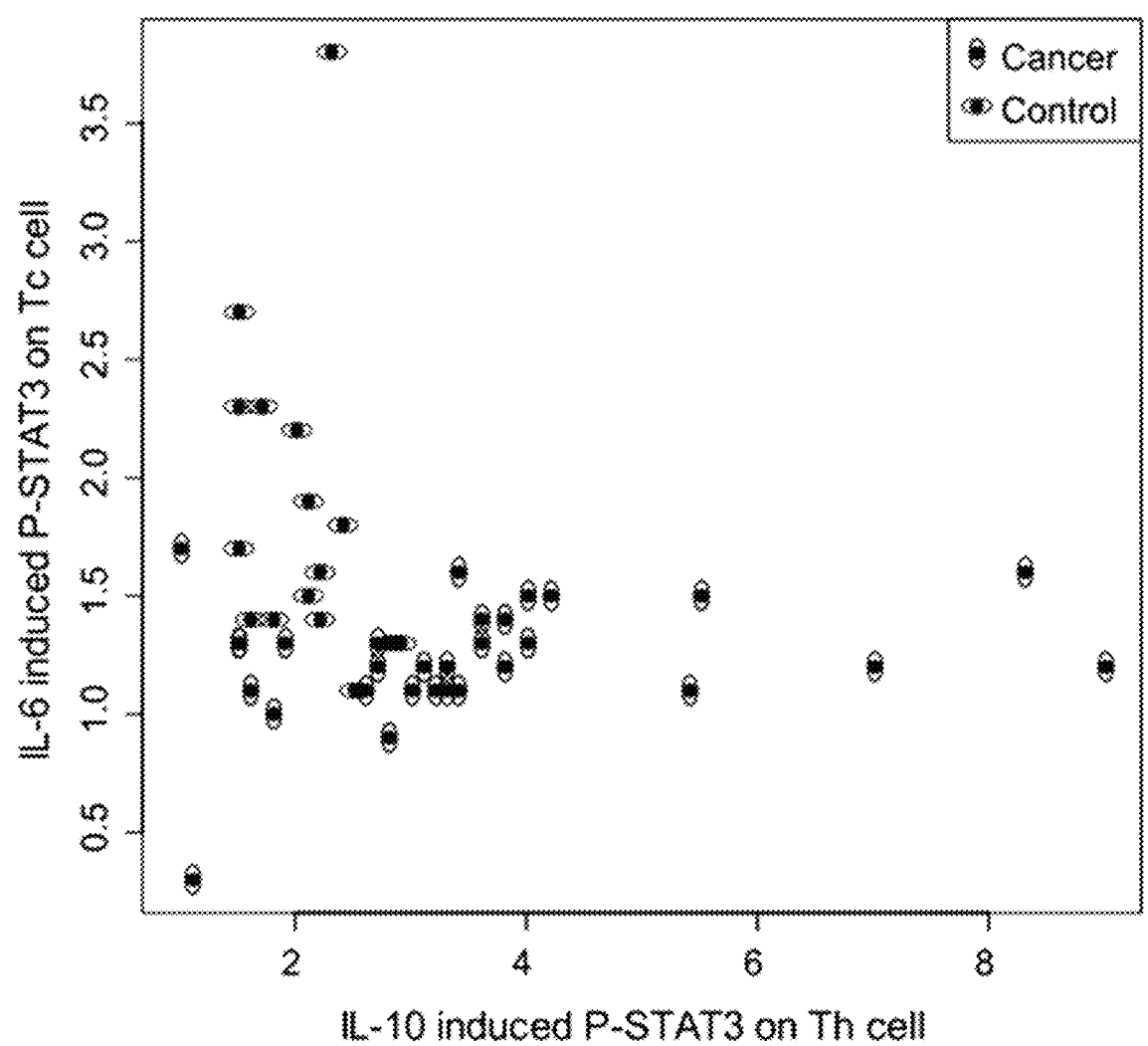
FIG. 9 is a schematic diagram of the distributions of colorectal cancer patients (red dots) and healthy persons (green dots) by using, as axes, respective items from cytokine and STAT combinations with largest differences (IL-6/pSTAT3 and IL-10/pSTAT3) found in the colorectal cancer patients and the healthy persons according to an embodiment of the present disclosure.

Analysis was performed using the principal component analysis package embedded in software through the R language, and the results are shown in FIGS. 8 and 9.

As can be seen from FIG. 8, there was different types of clustering between the colorectal cancer patient group and the normal person group. Especially, as confirmed in FIG. 9., the colorectal cancer patient group and the normal person group can be well distinguished by only the numerical values of IL-6-induced pSTAT3 on Tc cells and IL-10-induced pSTAT3 on Th cells.

Test Example: Statistical Method and Leave-One-Out Cross Validation (LOOCV)

Two CIPS patterns were identified through a statistical method and leave-one-out cross validation. Specifically, two features with the highest mean decrease Gini (MDG) value were selected among several CIPS features by using the random Forest package of R language, and a model was established using the logistic regression function embedded in R language. LOOCV was performed through R coding, and the ROCR package was utilized to plot an ROC curve. The results are shown in FIGS. 10 to 11.

Figure 10:
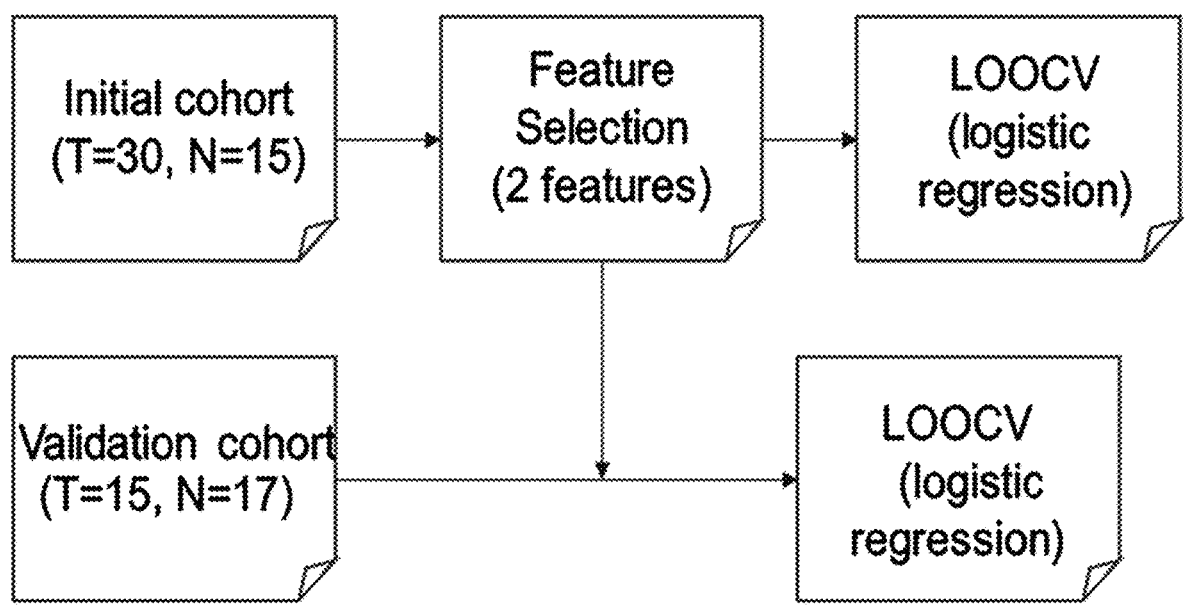
FIG. 10 is a schematic diagram showing a procedure wherein a statistical model was made by finding useful features for distinguishing between cancer patients and normal persons in training cohort and then validating the performance of the model through the use of validation cohort according to an embodiment of the present invention.
Figure 11:
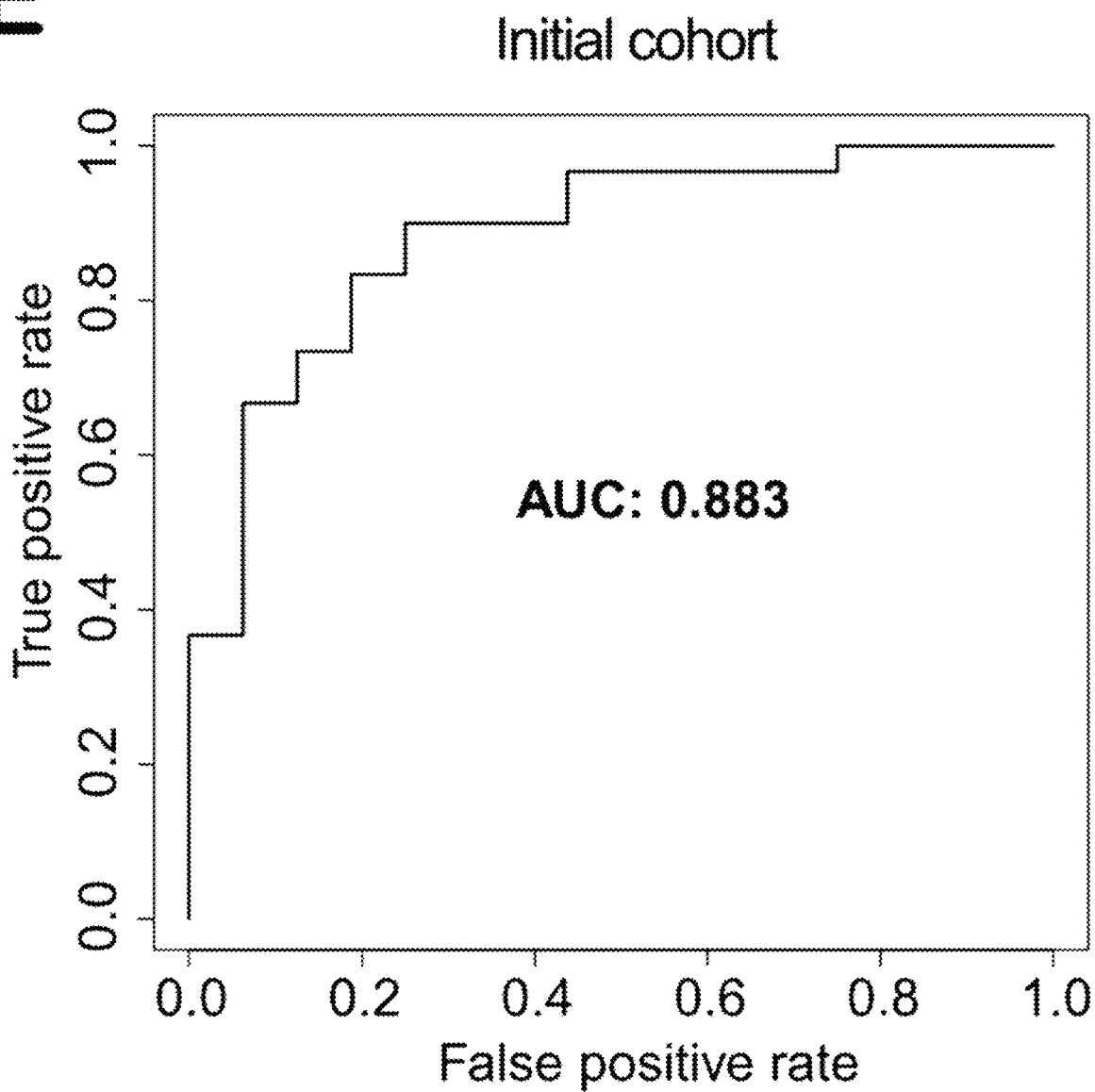
FIG. 11 shows the ROC analysis result depicting the performance of a statistical model using two features (IL-6/pSTAT3 and IL-10/pSTAT3) presented in this study in a training cohort according to an embodiment of the present invention.
Figure 12:
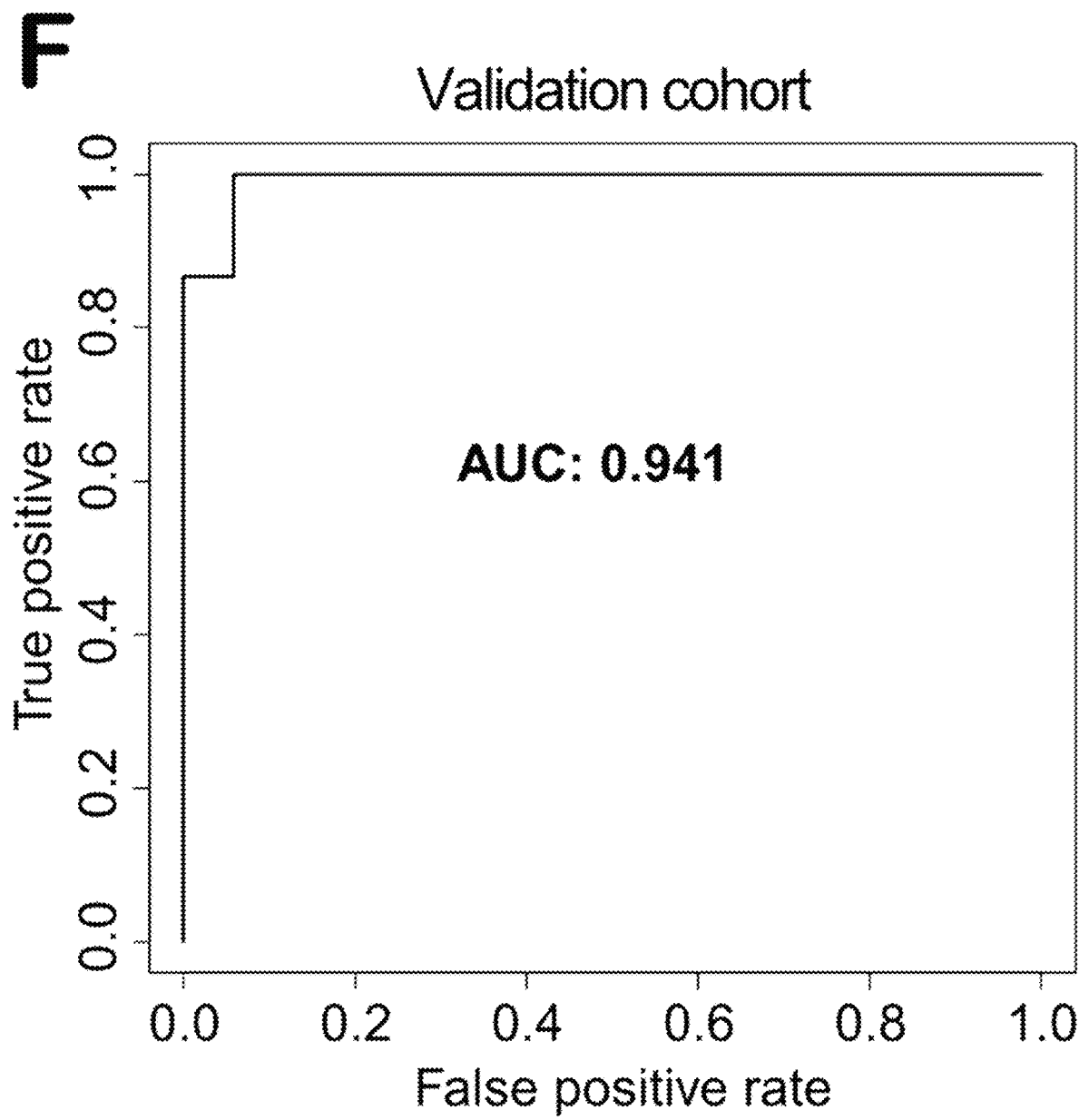
FIG. 12 shows the ROC analysis result depicting the performance of a statistical model using two features (IL-6/pSTAT3 and IL-10/pSTAT3) presented in this study in a validation cohort according to an embodiment of the present invention.

As can be confirmed from FIGS. 10 and 11, the use of IL-6-induced pSTAT3 on Tc cells and IL-10-induced pSTAT3 on Th cells can discriminate the tumor group and the normal group, and the AUC was 0.88. This was reproduced in the validation cohort with 15 CRC patients and 17 healthy persons (AUC 0.941). When training cohort and validation cohort were synthetically analyzed, the AUC was 0.938.

The discrimination between groups was analyzed by applying the carcinoembryonic antigen (CEA) protein marker, known as an existing CRC tumor marker, to both the two CIPS patterns, that is, IL-6-induced pSTAT3 on Tc cells and IL-10-induced pSTAT3 on Th cells. Specifically, it was predicted whether each patient was a cancer patient with a probability of 50% or more by using the previously established model, and the results were compared with the actually labeled (cancer patient vs. healthy person) values. The tumor patients were essentially tested for CEA, and thus the previously obtained test value and two markers derived in this experiment were analyzed by the same manner and model, and the results are shown in FIG. 13 and Table 16.

TABLE 16

|  | CRC patients | Health controls |
|---|---|---|
| Positive predicted | 41 | 4 |
| Negative predicted | 4 | 29 |

Figure 13:
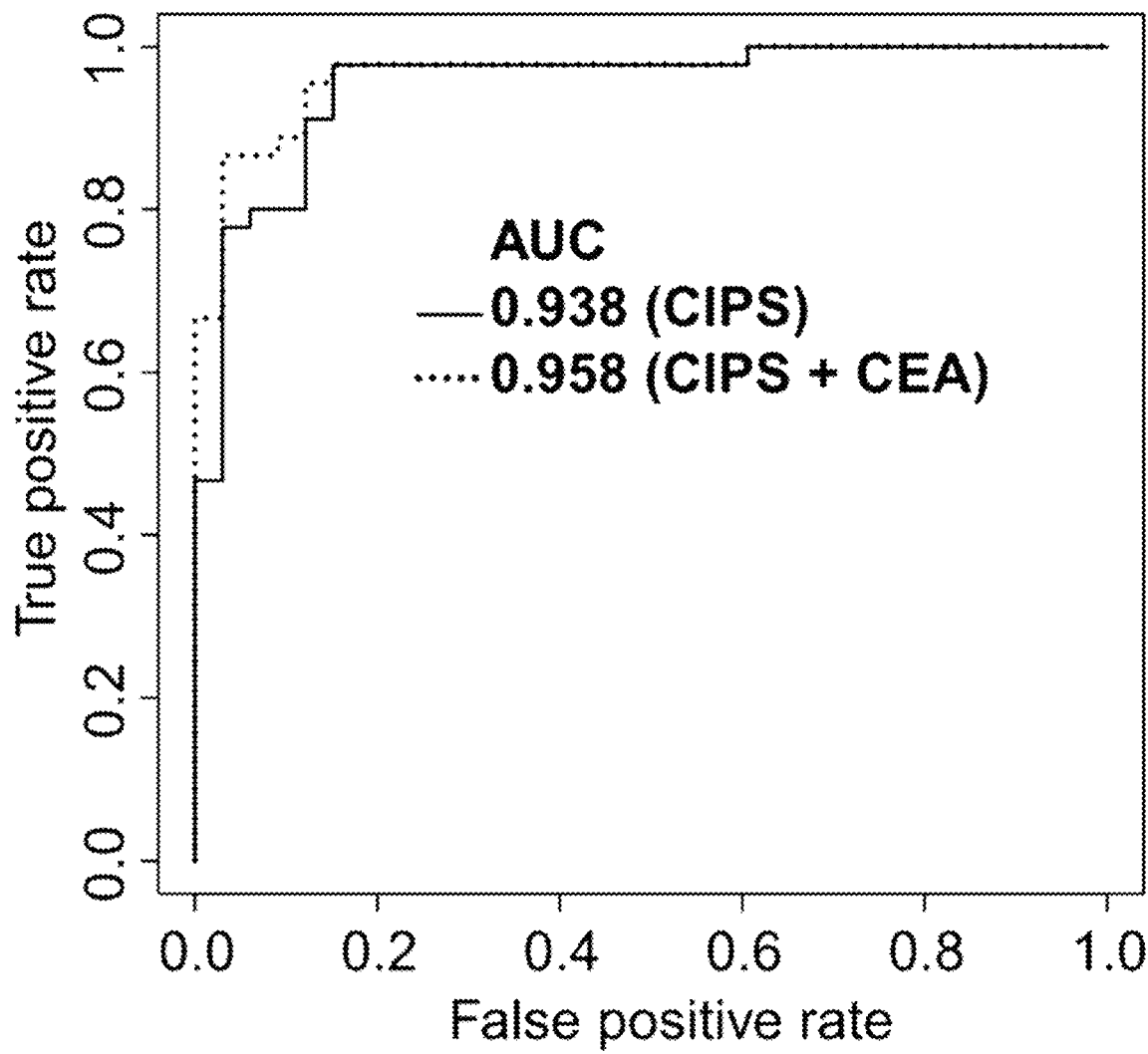
FIG. 13 shows the ROC analysis result depicting the performance of a statistical model using the two features (IL-6/pSTAT3 and IL-10/pSTAT3) presented in this study in training and validation cohorts (black line) and the ROC analysis result depicting the performance of a statistical model simultaneously employing the two features (IL-6/pSTAT3 and IL-10/pSTAT3) presented in this study in training and validation cohorts (red line) and a colorectal cancer marker (CEA) according to an embodiment of the present disclosure.

As can be seen from FIG. 13 and Table 16, the AUC was identified to be excellent, 0.958, proving that the diagnostic use of the two markers in combination can maximize the utility thereof. The positive and negative predictive values were shown as 91% and 88%, respectively.

Review

Combining the above results, it was confirmed that the measurement values of STAT phosphorylation by interleukin in immune T cells derived from blood were different between normal persons and colorectal cancer patients, and the combination of these values enables a technique capable of diagnosing a colorectal patient through the blood. Even the use of two markers in combination showed excellent performance with sensitivity of 91% and specificity of 88%, and the use thereof in combination with existing known colorectal cancer markers can further improve the diagnostic sensitivity and specificity thereof.

INDUSTRIAL APPLICABILITY

The present disclosure relates to a marker for diagnosing colorectal cancer, a method for providing information required for diagnosis of colorectal cancer by using the same, and a method for providing information for monitoring a therapeutic response of colorectal cancer by using the same.

What is claimed is:
1. A method for providing information required for the diagnosis of colorectal cancer, the method comprising:
measuring the level of signal transducer and activator of transcription 3 (STAT3) phosphorylation in helper T cells (Th cells) contained in a first sample; and
measuring the level of STAT3 phosphorylation in cytotoxic T cells (Tc cells) contained in a second sample,
wherein the first sample is prepared by:
a first mononuclear cell isolation step of isolating mononuclear cells contained in blood;
a first cytokine treatment step of treating the isolated mononuclear cells with IL-10; and
a first phosphorylation staining step of performing phosphorylation staining,
wherein the second sample is prepared by:
a second mononuclear cell isolation step of isolating mononuclear cells contained in blood;
a second cytokine treatment step of treating the isolated mononuclear cells with IL-6; and
a second phosphorylation staining step of performing phosphorylation staining.

2. The method of claim 1, wherein the first sample and the second sample include peripheral blood.

3. The method of claim 1, wherein the measuring of the level of STAT3 phosphorylation is performed using flow cytometry.

4. The method of claim 1, wherein the concentration of the IL-10 is 9.0 to 11.0 ng/ml.

5. The method of claim 1, wherein the concentration of the IL-6 is 19.0 to 21.0 ng/ml.

6. A method for providing information for monitoring a therapeutic response of colorectal cancer, the method comprising:

measuring the level of STAT3 phosphorylation in Th cells contained in a first sample; and measuring the level of STAT3 phosphorylation in Tc cells contained in a second sample, wherein the first sample is prepared by:

a first mononuclear cell isolation step of isolating mononuclear cells contained in blood;

a first cytokine treatment step of treating the isolated mononuclear cells with IL-10; and a first phosphorylation staining step of performing phosphorylation staining, wherein the second sample is prepared by:

a second mononuclear cell isolation step of isolating mononuclear cells contained in blood;

a second cytokine treatment step of treating the isolated mononuclear cells with IL-6; and a second phosphorylation staining step of performing phosphorylation staining.

7. The method of claim 6, wherein the first sample and the second sample are obtained from a patient who is being treated for colorectal cancer.

8. The method of claim 6, wherein the first sample and the second sample include peripheral blood.

9. The method of claim 6, wherein the measuring of the level of STAT3 phosphorylation is performed using flow cytometry.

10. The method of claim 6, wherein the concentration of the IL-10 is 9.0 to 11.0 ng/ml.

11. The method of claim 6, wherein the concentration of the IL-6 is 19.0 to 21.0 ng/ml.

* * * * *